United States Patent
Szakalas-Gratzl et al.

(10) Patent No.: US 11,684,573 B1
(45) Date of Patent: Jun. 27, 2023

(54) VASOPRESSIN LIQUID FORMULATIONS

(71) Applicant: Hikma Pharmaceuticals USA Inc., Eatontown, NJ (US)

(72) Inventors: Gyongyi Szakalas-Gratzl, Chagrin Fallls, OH (US); Ping Ma, Solon, OH (US); James Murtagh, Wilmington, NC (US)

(73) Assignee: HIKMA PHARMACEUTICALS USA INC., Eatontown, NJ (US)

( * ) Notice: Subject to any disclaimer, the term of this patent is extended or adjusted under 35 U.S.C. 154(b) by 0 days.

(21) Appl. No.: 16/902,648

(22) Filed: Jun. 16, 2020

Related U.S. Application Data

(60) Provisional application No. 62/862,168, filed on Jun. 17, 2019.

(51) Int. Cl.
| | |
|---|---|
| *A61K 9/08* | (2006.01) |
| *A61K 47/12* | (2006.01) |
| *A61K 38/095* | (2019.01) |
| *A61K 9/00* | (2006.01) |

(52) U.S. Cl.
CPC .............. *A61K 9/08* (2013.01); *A61K 9/0019* (2013.01); *A61K 38/095* (2019.01); *A61K 47/12* (2013.01)

(58) Field of Classification Search
CPC .......... A61K 38/11; A61K 9/00; A61K 47/12; A61K 9/08; A61K 9/0019; A61K 38/095
See application file for complete search history.

(56) References Cited

U.S. PATENT DOCUMENTS

| | | |
|---|---|---|
| 9,375,478 B1 | 6/2016 | Kenney et al. |
| 9,687,526 B2 | 6/2017 | Kenney et al. |
| 9,744,209 B2 | 8/2017 | Kenney et al. |
| 9,744,239 B2 | 8/2017 | Kenney et al. |
| 9,750,785 B2 | 9/2017 | Kenney et al. |
| 9,919,026 B2 | 3/2018 | Kenney et al. |
| 9,925,233 B2 | 3/2018 | Kenney et al. |
| 9,925,234 B2 | 3/2018 | Kenney et al. |
| 9,937,223 B2 | 4/2018 | Kenney et al. |
| 9,962,422 B2 | 5/2018 | Kenney et al. |
| 9,968,649 B2 | 5/2018 | Kenney et al. |
| 9,974,827 B2 | 5/2018 | Kenney et al. |
| 9,981,006 B2 | 5/2018 | Kenney et al. |
| 10,010,575 B2 | 7/2018 | Kenney et al. |

OTHER PUBLICATIONS

Akers, M.J. (Sterile Drug Products Formulation, Packaging, Manufacturing and Quality 2016 p. 99) (Year: 2016).*
Singh et al. (Ringer's Lactate 2021 [online] retrieved from: https://www.ncbi.nlm.nih.gov/books/NBK500033/; 5 pages). (Year: 2021).*
Visentini et al. (Abstract of: Rapid Commun Mass Spectrom 1989;3(11):390-5) 1 page (Year: 1989).*
Pharma pathway: Significant Change in Pharmaceutical Stability Testing [online] retrieved on Jul. 20, 2022 from: https://pharmapathway.com/significant-change-in-pharmaceutical-stability-testing/; Jun. 30, 2016: 2 pages. (Year: 2016).*
Bajaj et al. (Journal of Applied Pharmaceutical Science 2012;02(03):129-138)) (Year: 2012).*
Sizemore, et al., Adjusting vasopressin availability and formulation: A cost-savings initiative; Am. Jour. Health-System Pharm.; vol. 79, Issue Supplement_3; Sep. 1, 2022; Abstract.

* cited by examiner

*Primary Examiner* — Ernst V Arnold
(74) *Attorney, Agent, or Firm* — Pearne & Gordon LLP

(57) ABSTRACT

A liquid pharmaceutical composition for intravenous administration that includes vasopressin or a pharmaceutically acceptable salt thereof. The formulation further includes a lactate buffer or lactic acid, optionally in combination with a pH adjuster. The pharmaceutical composition can have a pH of from about 3.0 to about 4.1 and demonstrates improved stability for long term storage, particularly at room temperature.

39 Claims, No Drawings

VASOPRESSIN LIQUID FORMULATIONS

RELATED APPLICATIONS

This application claims the benefit of U.S. Provisional Application No. 62/862,168 filed Jun. 17, 2019, hereby incorporated by reference in its entirety.

TECHNICAL FIELD

The invention relates to a stable liquid formulation containing vasopressin as an active ingredient and, in particular, liquid formulations for intravenous infusion containing vasopressin and a lactate buffer having improved stability profiles.

BACKGROUND

Vasopressin is a hormone that is synthesized in the hypothalamus and is stored in and excreted by the pituitary gland. Its roles as both an osmolality regulator and as a neurotransmitter are well established, but vasopressin's role in increasing blood pressure by reduction of renal restriction at low concentrations and by vasoconstriction at higher concentrations has been clinically significant for decades. Vasopressin is currently marketed under the tradename VASOSTRICT® for the approved indication of increasing blood pressure in adults with vasodilatory shock (e.g. post-cardiotomy or sepsis who remain hypotensive despite fluids and catecholamines).

A nonapeptide, the structure of vasopressin is illustrated below. The chemical name is Cyclo (1-6) L-Cysteinyl-L-Tyrosyl-L-Phenylalanyl-LGlutaminyl-L-Asparaginyl-L-Cysteinyl-L-Prolyl-L-Arginyl-L-Glycinamide (MW=1084.23). At neutral or acidic pH, the two basic residues (Cys and Arg) are protonated and each can carry a counterion, often acetate or fluoroacetate.

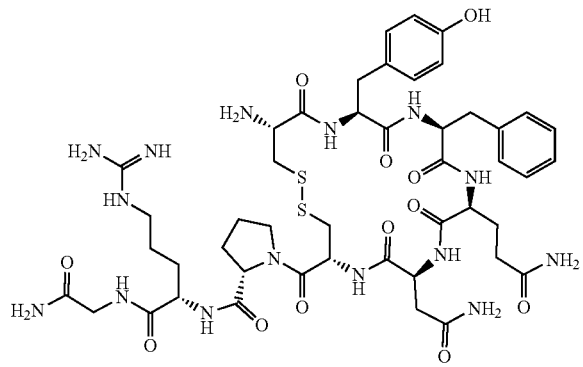 [SMILES: N=C(N)NCCC[C@H](NC(=O)[C@@H]1CCCN1C(=O)[C@@H]1CSSC[C@H](N)C(=O)N[C@@H](Cc2ccc(O)cc2)C(=O)N[C@@H](Cc2ccccc2)C(=O)N[C@@H](CCC(N)=O)C(=O)N[C@@H](CC(N)=O)C(=O)N1)C(=O)NCC(N)=O]

Vasopressin is available commercially under the tradename VASOSTRICT® and is formulated as an aqueous solution for dilution prior to intravenous solution. It is available in single dose vials (20 units/mL, 37.74 µg/mL) and multiple dose vials (200 units/10 mL, 37.74 µg/mL). Both the VASOSTRICT® single and multiple dose vials are formulated in an aqueous sodium acetate buffer adjusted to pH 3.8. The 10 mL solution additionally contains chlorobutanol (NF, 0.5%) as a preservative. Administration instructions on the product label instruct for dilution in normal saline (0.9% NaCl) or 5% dextrose in water (D5W) prior to administration. According to the product label, undiluted vials are to be stored between 2° C. and 8° C. Upon removal from refrigeration, vials can be stored at room temperature (20° C. to 25° C.) for up to 12 months. The label further instructs that vials should not be stored above 25° C.

There remains a need for liquid formulations for intravenous infusion with improved stability, and in particular, long-term room temperature storage stability. The present disclosure provides stable liquid formulations of vasopressin having minimal ingredients that exhibit enhanced storage stability as compared to the commercially available product.

SUMMARY

Described herein are liquid pharmaceutical compositions for intravenous administration that include vasopressin or pharmaceutically acceptable salts thereof and one or more of lactic acid or a lactate salt. The formulations exhibit improved stability at refrigerated and accelerated storage conditions compared to commercially available vasopressin formulations in acetate buffer.

In a first aspect, there is disclosed a liquid pharmaceutical composition for intravenous administration that includes vasopressin or a pharmaceutically acceptable salt(s) thereof, a lactic acid, a lactate salt, or combinations thereof. The composition further includes water. The composition optionally includes a pH adjuster.

In an example of the first aspect, the composition has a pH of from about 3.0 to about 4.1.

In another example of the first aspect, the composition has a pH of from about 3.2 to about 3.4.

In yet another example of the first aspect, the composition has a pH of about 3.3.

In another example of the first aspect, the lactic acid, lactate salt, or combination thereof is a lactate buffer.

In another example of the first aspect, the lactate buffer has a concentration of from about 1 µM to about 20 µM.

In yet another example of the first aspect, the lactate buffer has a concentration of from about 6 µM to about 14 µM.

In another example of the first aspect, the pharmaceutical composition is free of a non-lactate buffer.

In another example of the first aspect, the non-lactate buffer is an acetate buffer.

In another example of the first aspect, the vasopressin is a vasopressin salt selected from the group consisting of acetate or trifluoroacetate.

In another example of the first aspect, the pharmaceutical composition further comprises one or more pharmaceutically acceptable excipients.

In yet another example of the first aspect, the one or more pharmaceutically acceptable excipients includes a preservative.

In another example of the first aspect, the composition is preservative free.

In another example of the first aspect, the composition is stable for at least 12 months when stored at about 25° C. and about 60% relative humidity.

In another example of the first aspect, the composition is stable for at least 18 months when stored at about 25° C. and about 60% relative humidity.

In another example of the first aspect, the composition has a pH of from about 2.9 to about 4.1 and is stable for at least 12 months when stored at about 25° C. and about 60% relative humidity.

In another example of the first aspect, the composition has a pH of from about 3.2 to about 3.4 and is stable for at least 12 months when stored at about 25° C. and about 60% relative humidity.

In another example of the first aspect, the composition has a pH of about 3.3 and is stable for at least 12 months when stored at about 25° C. and about 60% relative humidity.

In another example of the first aspect, the composition is stable for at least 72 months when stored at about 5° C.

In another example of the first aspect, the composition has a pH of from about 2.9 to about 4.1 and is stable for at least 72 months when stored at about 5° C.

In another example of the first aspect, the composition has a pH of from about 3.0 to about 3.4 and is stable for at least 72 months when stored at about 5° C.

In yet another example of the first aspect, the composition has a pH of about 3.3 and is stable for at least 72 months when stored at about 5° C.

In another example of the first aspect, the composition contains a concentration of vasopressin or pharmaceutically acceptable salt thereof of between about 0.01 mg/mL and about 0.3 mg/mL.

In another example of the first aspect, the composition contains a concentration of vasopressin or pharmaceutically acceptable salt thereof of between about 0.02 mg/mL and about 0.07 mg/mL.

In another example of the first aspect, the composition contains a concentration of vasopressin or pharmaceutically acceptable salt thereof of between about 0.15 mg/mL and about 0.20 mg/mL.

In another example of the first aspect, the composition retains, as measured by HPLC, about 90% or more of the initial concentration of vasopressin or pharmaceutically acceptable salt thereof after storage at when stored at about 25° C. and about 60% relative humidity for about 6 months.

In another example of the first aspect, the composition retains, as measured by HPLC, about 95% or more of the initial concentration of vasopressin or pharmaceutically acceptable salt thereof after storage at when stored at about 25° C. and about 60% relative humidity for about 6 months.

In another example of the first aspect, after storage at about 5° C. for about 6 months, the pharmaceutical composition contains not more than about 2% of any individual degradant as measured by HPLC.

In another example of the first aspect, after storage at about 5° C. for about 6 months, the pharmaceutical composition contains not more than about 1% of any individual degradant as measured by HPLC.

In another example of the first aspect, after storage at about 25° C. and about 60% relative humidity for about 6 months, the pharmaceutical composition contains not more than about 3% of any individual degradant as measured by HPLC.

In yet another example of the first aspect, after storage at about 25° C. and about 60% relative humidity for about 6 months, the pharmaceutical composition contains not more than about 2% of any individual degradant as measured by HPLC.

In another example of the first aspect, the composition is stored in a glass vial.

In yet another example of the first aspect, the glass vial is a clear glass vial.

In another example of the first aspect is a method of increasing blood pressure in a mammal in need thereof by administering a pharmaceutical composition according to any of the foregoing examples.

In a second aspect of the disclosure is a pharmaceutical composition for intravenous administration. The pharmaceutical composition consists essentially of between 0.02 mg/mL and 0.05 mg/mL vasopressin or a pharmaceutically acceptable salt thereof. The composition further includes lactic acid, a lactate salt, or a combination thereof; water; and optionally, a pH adjuster. The pharmaceutical composition has a pH of from about 3.0 to about 3.7. After storage at about 25° C. and about 60% for at least 12 months, the pharmaceutical composition retains 90% or more of the initial concentration of vasopressin or pharmaceutically acceptable salt thereof as measured by HPLC.

In an example of the second aspect, the pharmaceutical composition has a pH of from about 3.2 to about 3.4.

In another example of the second aspect, the pharmaceutical composition retains 90% or more of the initial concentration of vasopressin or pharmaceutically acceptable salt thereof as measured by HPLC following storage for at least 18 months.

In an example of the second aspect is a method of increasing blood pressure in a mammal in need thereof by administering a pharmaceutical composition according to the second aspect.

In a third aspect of the disclosure is a pharmaceutical composition for intravenous administration. The pharmaceutical composition consists essentially of between 0.15 mg/mL and 0.25 mg/mL vasopressin or a pharmaceutically acceptable salt thereof. The composition further includes lactic acid, a lactate salt, or a combination thereof; water; and optionally, a pH adjuster. The pharmaceutical composition has a pH of from about 3.0 to about 3.7. After storage at about 25° C. and about 60% for about 12 months, the pharmaceutical composition retains 90% or more of the initial concentration of vasopressin or pharmaceutically acceptable salt thereof as measured by HPLC.

In another example of the third aspect, the pharmaceutical composition has a pH of from about 3.2 to about 3.4.

In another example of the second aspect, the pharmaceutical composition retains 90% or more of the initial concentration of vasopressin or pharmaceutically acceptable salt thereof as measured by HPLC following storage for at least 18 months.

In an example of the third aspect is a method of increasing blood pressure in a mammal in need thereof by administering a pharmaceutical composition according to the third aspect.

In a fourth aspect of the disclosure is a method of increasing blood pressure in a patient in need thereof. The method includes the steps of providing a pharmaceutical composition and intravenously administering the pharmaceutical composition to the patient. The pharmaceutical composition includes vasopressin or a pharmaceutically acceptable salt thereof; lactic acid, a lactate salt, or a combination thereof; water; and optionally, a pH adjuster. After storage at about 25° C. and 60% relative humidity for about 6 months, the pharmaceutical composition retains 90% or more of the initial vasopressin concentration.

In an example of the fourth aspect, the composition has a pH of from about 3.0 to about 4.1.

In another example of the fourth aspect, the composition has a pH of from about 3.2 to about 3.4.

In yet another example of the fourth aspect, the composition has a pH of about 3.3.

In another example of the fourth aspect, the composition retains, as measured by HPLC, 90% or more of the initial concentration of vasopressin or pharmaceutically acceptable salt thereof after storage at when stored at about 25° C. and about 60% relative humidity for about 12 months.

In another example of the fourth aspect, the composition retains, as measured by HPLC, 90% or more of the initial concentration of vasopressin or pharmaceutically acceptable salt thereof after storage at when stored at about 25° C. and about 60% relative humidity for about 18 months.

In another example of the fourth aspect, the pharmaceutical composition is free of a non-lactate buffer.

In yet another example of the fourth aspect, the pharmaceutical composition is free of an acetate buffer.

DETAILED DESCRIPTION

As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors. When the term "about" is used in describing a value or an end-point of a range, the disclosure should be understood to include the specific value or end-point referred to. Whether or not a numerical value or end-point of a range in the specification recites "about," the numerical value or end-point of a range is intended to include two embodiments: one modified by "about," and one not modified by "about." It will be further understood that the endpoints of each of the ranges are significant both in relation to the other endpoint, and independently of the other endpoint and that ranges include both of the endpoints as well as each of the discreet values therein.

The terms "substantial," "substantially," and variations thereof as used herein are intended to note that a described feature is equal or approximately equal to a value or description. Moreover, "substantially" is intended to denote that two values are equal or approximately equal. In some embodiments, "substantially" may denote values within about 10% of each other, for example within about 5% of each other, or within about 2% of each other.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

The present disclosure is directed to stable liquid formulations for intravenous administration that include vasopressin, or a pharmaceutically acceptable salt thereof, in a lactate buffer comprising a lactate salt and/or lactic acid, and optionally, a pH adjuster such as sodium hydroxide, hydrochloric acid or lactic acid. The lactate-buffered vasopressin formulations of the current disclosure demonstrate the highest stability when buffered to a pH of from about 3.0 to 4.1.

The formulations of vasopressin of the present disclosure can be for intravenous or parenteral administration. In some examples, the formulations are ready-to-use or ready-to-administer formulations such as a liquid stored in a pharmaceutically suitable container, for example, a glass vial or plastic intravenous bag. A ready-to-use or ready-to-administer formulation is a sterile, liquid injectable formulation not requiring reconstitution before use such that the formulation can be further diluted if present as a concentrated solution, or directly administered. For example, a ready-to-administer formulation can be included at the required concentration and volume in the final container such as a syringe or injector. A ready-to-use preparation can be at the required concentration and a volume in a container that may be transferred to a final administration device such as a syringe or infusion bag for administration to a patient. Diluents can include, for instance, fluids suitable for parenteral administration such as sodium chloride or dextrose solutions. In one example, the pharmaceutical composition is a ready-to-use preparation.

The pharmaceutical compositions provided herein may be formulated for single or multiple dosage administration. Multiple dosage formulations may include an antimicrobial agent at bacteriostatic or fungistatic concentrations. All formulations must be sterile, as known and practiced in the art.

The liquid formulations of the present disclosure are stable or exhibit stability when stored, which includes formulation properties that may be affected by storage conditions, for example, active ingredient strength or concentration, impurities (e.g., individual components and total), visual appearance characteristics (e.g., color, clarity, cloudy, haze, precipitates, etc.) and viscosity. Storage conditions that may affect stability can include, for example, storage temperature, humidity (e.g., relative), light exposure and storage time period.

In one or more embodiments, stability can include the amount of total impurities, inclusive of degradation products, that are formed after formation of the vasopressin formulation for a specified period of time at specified storage conditions (e.g., temperature, humidity) minus the initial total impurities as measured following formation (i.e. the baseline or initial impurity measurement). As used herein, "stability" or a "stable formulation" refers to a formulation demonstrating one or more of the following characteristics upon inspection. The formulations can be examined visually. Stable formulations are clear, colorless solutions that are free or essentially free from visible signs of contamination from any foreign materials and/or particulate matter. The formulations can be tested for pH stability over time. By this measure, formulations are deemed to be stable when the pH varies less than ±0.2 pH units, preferably less than ±0.15 pH units, over the period of storage. The formulations can also be measured for chromatographic (HPLC) purity using relative peak areas determined from a standard set of run parameters. First, following a period of storage, the relative value of vasopressin remaining in the formulation as compared to a known amount of vasopressin (e.g. a vasopressin standard) can be measured (referred to as "Assay %"). Stable samples according to the Assay % should demonstrate 90.0 to 110.0% (±10.0%) vasopressin remaining relative to standard as a measure of peak areas. Another chromatographic test (referred to as "Chromatographic purity (%)") measures the peak area of the vasopressin peak relative to the total peak chromatographic peak area. By this measurement, stable formulations retain 90.0% or greater of the original vasopressin concentration by chromatographic determination. In some aspects, stable formulations are those formulations demonstrating visual stability over the storage period. In some examples, stable formulations are those formulations that maintain pH stability over the storage period. In other examples, stable formulations are those formulations that demonstrate stability by one or more chromatographic assay(s) over the storage period. In other examples, stable formulations according to the present disclosure are those formulations demonstrating two or more of visual stability, pH stability, and chromatographic stability over the storage period. In yet other examples, stable formulations demonstrate all of visual stability, pH stability, and chromatographic stability over the storage period.

In one or more embodiments, a liquid vasopressin formulation includes a formulation that retains 90.0% or more, about 91.0% or more, about 92.0% or more, about 93.0% or more, about 94.0% or more, about 95.0% or more, about 96.0% or more, about 97.0% or more, about 98.0% or more, or about 99.0% or more of the initial concentration of vasopressin or pharmaceutically acceptable salt thereof in the formulation after storage under standard (e.g., about 5° C., or "refrigerated" conditions), room temperature (e.g., about 15° C. to about 30° C., including about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., or any range in between), or accelerated conditions (e.g., about 25° C./60% Relative Humidity (RH), about 30° C./65% RH, about 40° C./75% RH, etc.). The initial concentration of vasopressin or a pharmaceutically acceptable salt can be measured shortly after formation and filling of the formulation into a pharmaceutically acceptable container (e.g., a vial) prior to storage. For example, filling of the formulation can be within 1-24 hours of formation of the formulation. In one or more embodiments, a stable vasopressin formulation includes a formulation that contains about 0.25% or less, about 0.5% or less, about 0.75% or less, about 1.0% or less, about 1.5% or less, about 2.0% or less, about 2.5% or less, or about 3.0% or less of an individual degradant (e.g., a degradation product) formed after formation of the formulation and present after storage under standard, room temperature, or accelerated conditions (e.g., about 5° C., 25° C./60% RH, 30° C./65% RH, 40° C./75% RH or 50° C.) for about 1 week, about 2 weeks, about 3 weeks, about 4 weeks (1 month), about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, or about 18 or more months. Any measured individual impurity or degradant for purposes of measuring stability of a formulation herein does not include any impurity or degradant present in any ingredient prior to formation of the vasopressin formulation. That is, as used herein, an impurity, impurities, degradant or degradants in a formulation according to the present disclosure refers to any impurity or degradation product formed after formation of the formulation.

In one or more embodiments, a liquid vasopressin formulation includes a formulation that is stable for about 3 months or more, about 6 months or more, about 9 months or more, about 12 months or more, or about 18 months or more when stored at an accelerated temperature of about 25° C./60% RH or about 30° C./65% RH. In one or more embodiments, a liquid vasopressin formulation includes a formulation that is stable for about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months or more when stored at room temperature accelerated conditions (i.e. 25±2° C., 60±5% RH).

The formulations of the present disclosure contain, as the active ingredient, vasopressin or any pharmaceutically acceptable salt thereof. In some embodiments, the formulations preferably contain vasopressin or any pharmaceutically acceptable salt thereof as the sole active ingredient characterized in that no other active ingredients are present in the formulation. In one example, the formulation contains vasopressin acetate. In another example, the vasopressin salt can be vasopressin fluoroacetate.

The pharmaceutical composition (or formulation) may be administered intravenously and contains a therapeutically effective amount of vasopressin. As described herein, a therapeutically effective amount can be present in a composition at a concentration of vasopressin, for example, about 0.1 units/mL, about 0.2 units/mL, about 0.3 units/mL, about 0.4 units/mL, about 0.5 units/mL, about 0.6 units/mL, about 0.7 units/mL, about 0.8 units/mL, about 0.9 units/mL, about 1.0 units/mL, about 2.0 units/mL, about 3.0 units/mL, about 4.0 units/mL, about 5.0 units/mL, about 6.0 units/mL, about 7.0 units/mL, about 8.0 units/mL, about 9.0 units/mL, about 10 units/mL, about 15 units/mL, about 20 units/mL, about 30 units/mL, about 40 units/mL, about 50 units/mL, about 60 units/mL, about 70 units/mL, about 80 units/mL, about 90 units/mL, about 100 units/mL, about 110 units/mL, about 120 units/mL, about 130 units/mL, about 140 units/mL, about 150 units/mL, about 160 units/mL, about 170 units/mL, about 180 units/mL, about 190 units/mL, about 200 units/mL, about 210 units/mL, about 220 units/mL, about 230 units/mL, about 240 units/mL, about 250 units/mL, about 260 units/mL, about 270 units/mL, about 280 units/mL, about 290 units/mL, or about 300 units/mL.

A therapeutically effective amount of vasopressin can be present in an amount of, for example, about 0.01 µg, about 0.02 µg, about 0.03 µg, about 0.04 µg, about 0.05 µg, about 0.06 µg, about 0.07 µg, about 0.08 µg, about 0.09 µg, about 0.1 µg, about 0.11 µg, about 0.12 µg, about 0.13 µg, about 0.14 µg, about 0.15 µg, about 0.16 µg, about 0.17 µg, about 0.18 µg, about 0.19 µg, about 0.2 µg, about 0.3 µg, about 0.4 µg, about 0.5 µg, about 0.6 µg, about 0.7 µg, about 0.8 µg, about 0.9 µg, about 1.0 µg, about 1.5 µg, about 2.0 µg, about 2.5 µg, about 3.0 µg, about 3.5 µg, about 4.0 µg, about 4.5 µg, about 5.0 µg, about 5.5 µg, about 6.0 µg, about 6.5 µg, about 7.0 µg, about 7.5 µg, about 8.0 µg, about 8.5 µg, about 9.0 µg, about 9.5 µg, about 10 µg, about 20 µg, about 30 µg, about 40 µg, about 50 µg, about 60 µg, about 70 µg, about 80 µg, about 90 µg, about 100 µg, about 120 µg, about 140 µg, about 160 µg, about 180 µg, about 200 µg, about 220 µg, about 240 µg, about 260 µg, about 280 µg, about 300 µg, about 320 µg, about 340 µg, about 360 µg, about 380 µg, about 400 µg, about 420 µg, about 440 µg, about 460 µg, about 480 µg, about 500 µg, about 520 µg, about 540 µg, about 560 µg, about 580 µg, about 600 µg, about 620 µg, about 640 µg, about 660 µg, about 680 µg, about 700 µg, about 720 µg, about 740 µg, about 760 µg, about 780 µg, about 800 µg, about 820 µg, about 840 µg, about 860 µg, about 880 µg, about 900 µg, about 920 µg, about 940 µg, about 960 µg, about 980 µg, or about 1 mg.

A therapeutically effective amount of vasopressin can be present in a concentration of, for example, about 0.001 mg/mL, about 0.002 mg/mL, about 0.003 mg/mL, about 0.004 mg/mL, about 0.005 mg/mL, about 0.006 mg/mL, about 0.007 mg/mL, about 0.008 mg/mL, about 0.009 mg/mL, about 0.01 mg/mL, about 0.015 mg/mL, about 0.02 mg/mL, about 0.025 mg/mL, about 0.03 mg/mL, about 0.035 mg/mL, about 0.04 mg/mL, about 0.045 mg/mL, about 0.05 mg/mL, about 0.055 mg/mL, about 0.06 mg/mL, about 0.065 mg/mL, about 0.07 mg/mL, about 0.075 mg/mL, about 0.08 mg/mL, about 0.085 mg/mL, about 0.08 mg/mL, about 0.085 mg/mL, about 0.09 mg/mL, about 0.095 mg/mL, about 0.1 mg/mL, about 0.15 mg/mL, about 0.2 mg/mL, about 0.25 mg/mL, about 0.3 mg/mL, about 0.35 mg/mL, about 0.4 mg/mL, about 0.45 mg/mL, about 0.5 mg/mL, about 0.55 mg/mL, about 0.6 mg/mL, about 0.65 mg/mL, about 0.7 mg/mL, about 0.75 mg/mL, about 0.8 mg/mL, about 0.85 mg/mL, about 0.9 mg/mL, about 0.95 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, or about 10 mg/mL.

In addition to the active pharmaceutical ingredient, formulations of the present disclosure include a buffer or buffering agent. Suitable buffers or buffering agents include lactic acid, or a lactate salt having a pH of between about 2.5 and 4.5, preferably between 3.0 and 4.1. The concentration of the buffer can range from about 0.1 mM to about 100 mM, for example, about 0.1 mM, about 0.5 mM, about 1.0 mM, about 1.5 mM, about 2.0 mM, about 2.5 mM, about 3.0 mM, about 3.5 mM, about 4.0 mM, about 4.5 mM, about 5.0 mM, about 5.5 mM, about 6.0 mM, about 6.5 mM, about 7.0 mM, about 7.5 mM, about 8.0 mM, about 8.5 mM, about 9.0 mM, about 9.5 mM, about 10.0 mM, about 10.5 mM, about 11.0 mM, about 11.5 mM, about 12.0 mM, about 12.5 mM, about 13.0 mM, about 13.5 mM, about 14.0 mM, about 14.5 mM, about 15.0 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM or about 100 mM. The buffer for use with the formulations disclosed herein can be a premixed buffer or can be made in situ as part of the formulation process. In some examples, lactic acid or lactate salt is the only buffer present in the composition. That is, the composition is free of a non-lactic acid or lactate buffer. In some examples, the composition is substantially free of an acetate buffer. In some examples, the composition is free of an acetate buffer.

The formulations can be supplied or stored in any suitable volume for intravenous administration or for dilution prior to intravenous administration. In one or more embodiments, the formulation volume (e.g., amount of liquid in a storage container) is between about 0.1 mL and about 1000 mL. For example, the formulation volume can be about 0.1 mL to about 10 mL, about 0.5 mL to about 5 mL, or about 1 mL. In some embodiments, the formulation volume is about 1 mL, about 2 mL, about 3 mL, or about 5 mL. In one example, the formulation volume is about 1 mL. Appropriate-sized containers for storing formulation volumes can be determined by one of ordinary skill in the art.

The formulations can be stored in or supplied in any suitable container. For example, the formulation can be in a container that includes, but is not limited to, a vial, ampoule, bag (IV bag), bottle, or syringe (e.g., pre-filled syringe or component of an auto-injector). The container can be made of any suitable material, for instance, glass, plastic, or rubber. Prior to filling the formulation in a container, the container is preferably sterile and has been subjected to a sterilization process prior to filling with the sterile formulations of the invention. Formulations may also be subject to sterilization after filling of the vials or other containers. Containers are sealed as typical in the industry, for example, with the use of a lid, cap, closure, stopper and the like. The containers also can be coated or treated with one or more components to reduce reaction with ingredients of the formulation. For example, a container surface in contact with the formulation can be coated with silicon or a vial with a treated inner surface for storing the formulation can be used. To shield the formulation from exposure to light, a container can optionally be opaque or tinted with a color, and optionally stored in a box or other packaging for transport or shelving.

The formulations can further include a pH adjuster, for example, an acid or a base. The pH adjuster serves to aid in adjusting the pH of the aqueous formulation. In one or more embodiments, the pH adjuster is hydrochloric acid. In one or more embodiments, the pH adjuster is glacial acetic acid. In one or more embodiments, the pH adjuster is sodium hydroxide. In another embodiment, the pH adjusting agent can be lactic acid. The concentration of the pH adjuster can be any concentration suitable for adjusting the pH, such as, for example, 1 N acid or base. The formulation can have any suitable acidic pH. In an example, the formulation can have a pH of about 2.5, about 2.6, about 2.7, about 2.8, about 2.9, about 3.0 about 3.1, about 3.2, about 3.3, about 3.4, about 3.5, about 3.6, about 3.7, about 3.8, about 3.9, about 4.0, about 4.1, about 4.2, about 4.3, about 4.4, or about 4.5. In one or more embodiments, the formulation can have a pH in the range of about 3.1 to about 4.1, about 3.2 to about 4.1, about 3.3 to about 4.1, about 3.4 to about 4.1, about 3.5 to about 4.1, about 3.6 to about 4.1, about 3.7 to about 4.1, about 3.8 to about 4.1, about 3.9 to about 4.1 or about 4.0 to about 4.1. In another example, the pH of the formulation is the range of from about 3.0 to about 3.6, about 3.1 to about 3.6, about 3.2 to about 3.6, about 3.3 to about 3.6, about 3.4 to about 3.6, about 3.5 to about 3.6. In other examples, the pH of the formulation is about 3.0, about 3.1, about 3.2, about 3.3, about 3.4, about 3.5, about 3.6, about 3.7, about 3.8, about 3.9, about 4.0, or about 4.1.

Optional ingredients for formulating liquid formulations, such as diluents, salts, tonicity agents, antioxidants, and preservatives, can be provided to the formulation at any stage in its preparation.

The formulations of the present disclosure are suitable for intravenous administration, for example, to a mammal to treat or prevent a disease or condition. Preferably, the mammal is a human. The disease or condition is treatable by the administration of vasopressin or a pharmaceutically acceptable salt thereof. In an example, the pharmaceutical composition is administered to increase blood pressure in a patient. In particular, the formulations of the present disclosure can be administered to patients with vasodilatory shock requiring an increase in blood pressure.

In order to demonstrate the practice of the present invention, the following examples have been prepared and tested. The examples should not, however, be viewed as limiting the scope of the invention. The claims will serve to define the invention.

EXAMPLES

Example 1—Comparative Example: Stability Determination for Vasopressin in Acetate Buffer Formulations This comparative example demonstrates the stability of formulations comprising vasopressin acetate in acetate buffer. Vasopressin formulations were made to include 20 units/mL (37.74 μg/mL) vasopressin, 10 mM acetate buffer. The pH was adjusted to 2.9, 3.3, 3.7, 4.1 and 4.5 with 1N HCl and/or 1N NaOH. The formulations were stored in a 2 cc blow back, clear, Type I glass vials with 13 mm, 4432/50 Grey West (Teflon 2 coating) Westar Silicone stoppers. The filter membrane was a Millipore Durapore PVDF disk membrane with a 0.22 μm pore size and 47 mm diameter. Flush volumes were applied to compensate for peptide surface adsorptions. The fill volume was 1 mL. All vials were stored in upright positions under the storage conditions set forth in the examples below.

At set periods of storage time, the stability of the formulations was assessed in several different ways. As used herein, a formulation that is "stable", or a "stable formulation" is a formulation demonstrating stability according to two or more of the following tests. First, vials were visually inspected ensure they remained as clear, colorless solutions free of particulate matter. "MR" as used in the tables below stands for "Meets Requirement," which is a clear, colorless solution free or essentially free of visible signs of contamination from any foreign materials and/or particulate matter. Second, the pH of each formulation sample was measured.

Stable pH values were deemed to be those that varied less than ±0.2 pH units, preferably less than ±0.15 pH units, over the period of storage. Third, the formulations were tested for chromatographic (HPLC) purity in two different manners. The chromatographic assay ("Assay %" values indicated in the tables below) measured the relative value of vasopressin remaining in the formulation as compared to a known amount of standard. Stable samples as measured demonstrated 90.0 to 110.0% (±10.0%) vasopressin remaining relative to standard as a measure of peak area of vasopressin compared to the peak area of a known standard. A second chromatographic test ("Chromatographic purity (%)") monitored the peak area of the vasopressin peak relative to the total peak chromatographic peak areas. By this measurement, formulations containing 90.0% or greater of the original vasopressin concentration by chromatographic determination were deemed to be stable. The best performing formulations (i.e. most stable) were those that were stable upon visual inspection, pH measurement and by one or both chromatographic test(s). Preferably, stable formulations demonstrated pH stability, assay % stability and chromatographic purity stability.

The HPLC conditions for each of the chromatographic assays were as follows: Column: Phenomenex Aeris Peptide, 3.6 µm, 4.6×250 mm, P/N 00G-4507-E0; Mobile phase A: 5.94 g of dibasic ammonium phosphate dissolved in purified water, pH adjusted to 2.1±0.05 with o-phosphoric acid, total volume of 1000 mL; Mobile Phase B: acetonitrile; Diluent: 0.025% v/v glacial acetic acid in water; Column temperature: 35° C.; Flow rate: 1.0 mL/min; Injection volume: 16-80 µL; Autosampler temperature: 5° C.; Separation mode: gradient; Gradient program:

| Time (min) | % Mobile phase A | % Mobile phase B |
|---|---|---|
| 0 | 89 | 11 |
| 20 | 80 | 20 |
| 24 | 60 | 40 |
| 25 | 89 | 11 |
| 35 | 89 | 11 |

Using the above conditions, the relative retention time (RRT) of vasopressin is approximately 9.5 minutes.

Table 1 below sets forth the stability results of vasopressin formulations in acetate buffer prepared as described above having pH 2.5, 2.9, 3.3, 3.7, 4.1 and 4.5. The formulations were stored at 5±3° C. for 1 week, 2 weeks, 3 weeks, 4 weeks, 3 months and 6 months.

TABLE 1

Stability of vasopressin formulations in acetate buffer following extended storage of 5 ± 3° C. as a function of pH

| pH | Testing | $T_0$ | 1 wk | 2 wks | 3 wks | 4 wks | 3 mo | 6 mo |
|---|---|---|---|---|---|---|---|---|
| 2.5 | Appearance | MR | MR | MR | MR | MR | MR | MR |
|  | pH | 2.62 | 2.71 | 2.67 | 2.69 | 2.71 | 2.62 | 2.79 |
|  | Assay % | 101.3 | 99.4 | 99.8 | 101.0 | 100.5 | 98.1 | 99.0 |
|  | Chromatographic purity (%) | 98.83 | 98.82 | 98.75 | 98.57 | 98.60 | 97.83 | 97.23 |
| 2.9 | Appearance | MR | MR | MR | MR | MR | MR | MR |
|  | pH | 2.96 | 3.15 | 3.10 | 3.12 | 3.07 | 3.09 | 3.19 |
|  | Assay % | 101.5 | 99.6 | 100.1 | 100.7 | 100.8 | 98.8 | 98.1 |
|  | Chromatographic purity (%) | 99.25 | 99.13 | 99.21 | 99.18 | 99.14 | 98.78 | 98.41 |
| 3.3 | Appearance | MR | MR | MR | MR | MR | MR | MR |
|  | pH | 3.30 | 3.53 | 3.47 | 3.49 | 3.49 | 3.50 | 3.61 |
|  | Assay % | 101.1 | 98.8 | 99.6 | 101.0 | 100.5 | 98.4 | 98.3 |
|  | Chromatographic purity (%) | 99.39 | 99.40 | 99.35 | 99.39 | 99.27 | 99.27 | 99.13 |
| 3.7 | Appearance | MR | MR | MR | MR | MR | MR | MR |
|  | pH | 3.69 | 3.84 | 3.86 | 3.83 | 3.83 | 3.79 | 3.92 |
|  | Assay % | 101.4 | 99.1 | 100.1 | 101.2 | 100.8 | 98.8 | 97.0 |
|  | Chromatographic purity (%) | 99.57 | 99.36 | 99.57 | 99.53 | 99.47 | 99.36 | 99.05 |
| 4.1 | Appearance | MR | MR | MR | MR | MR | MR | MR |
|  | pH | 4.13 | 4.22 | 4.22 | 4.23 | 4.19 | 4.19 | 4.34 |
|  | Assay % | 101.1 | 99.9 | 99.8 | 101.0 | 100.6 | 96.7 | 99.5 |
|  | Chromatographic purity (%) | 99.40 | 99.45 | 99.36 | 99.52 | 99.41 | 99.13 | 99.29 |
| 4.5 | Appearance | MR | MR | MR | MR | MR | MR | MR |
|  | pH | 4.51 | 4.57 | 4.60 | 4.58 | 4.57 | 4.43 | 4.64 |
|  | Assay % | 101.0 | 99.6 | 100.0 | 101.0 | 99.3 | 97.7 | 100.7 |
|  | Chromatographic purity (%) | 99.5 | 99.4 | 99.42 | 99.44 | 99.44 | 99.18 | 99.2 |

As seen from Table 1, vasopressin formulations in acetate buffer having pH 2.5, 2.9, 3.3, 3.7, 4.1 and 4.5 were all stable by appearance and by both chromatographic tests at 3 months when stored at about 5° C. The pH monitoring showed a greater than optimal variation of the solution having pH 3.3 at the 1 week time point (+0.23 pH units). By 6 months, all of the formulations having a pH of 2.9 or greater had less than acceptable pH drift. That is, following 6 months of storage, no acetate formulation having a pH of 2.9 or greater passes the pH monitoring assay.

Table 2 below sets forth the stability results of vasopressin formulations in acetate buffer prepared as described above having pH 2.5, 2.9, 3.3, 3.7, 4.1 and 4.5. Formulations were stored at 25±2° C., 60±5% RH for 1 week, 2 weeks, 3 weeks, 4 weeks, 3 months and 6 months.

TABLE 2

Stability of vasopressin formulations in acetate buffer following extended storage of 25 ± 2° C., 60 ± 5% RH as a function of pH

| pH | Testing | $T_0$ | 1 wk | 2 wks | 3 wks | 4 wks | 3 mo | 6 mo |
|---|---|---|---|---|---|---|---|---|
| 2.5 | Appearance | MR | MR | MR | MR | MR | MR | MR |
|  | pH | 2.62 | 2.74 | 2.66 | 2.69 | 2.70 | 2.68 | 2.89 |
|  | Assay % | 101.3 | 99.1 | 98.5 | 98.8 | 98.1 | 90.2 | 83.6 |
|  | Chromatographic purity (%) | 98.83 | 98.3 | 97.46 | 96.77 | 96.11 | 89.87 | 83.70 |
| 2.9 | Appearance | MR | MR | MR | MR | MR | MR | MR |
|  | pH | 2.96 | 3.16 | 3.08 | 3.08 | 3.12 | 3.16 | 3.24 |
|  | Assay % | 101.5 | 99.4 | 98.9 | 100.2 | 99.0 | 94.9 | 92.0 |
|  | Chromatographic purity (%) | 99.25 | 98.96 | 98.70 | 98.43 | 98.06 | 95.81 | 93.11 |
| 3.3 | Appearance | MR | MR | MR | MR | MR | MR | MR |
|  | pH | 3.30 | 3.53 | 3.52 | 3.50 | 3.50 | 3.39 | 3.68 |
|  | Assay % | 101.1 | 99.1 | 98.4 | 100.2 | 99.6 | 96.6 | 94.0 |
|  | Chromatographic purity (%) | 99.39 | 99.2 | 99.07 | 99.05 | 98.88 | 97.76 | 96.32 |
| 3.7 | Appearance | MR | MR | MR | MR | MR | MR | MR |
|  | pH | 3.69 | 3.84 | 3.88 | 3.81 | 3.78 | 3.80 | 3.95 |
|  | Assay % | 101.4 | 98.8 | 98.6 | 100.2 | 100.0 | 96.1 | 94.4 |
|  | Chromatographic purity (%) | 99.57 | 99.36 | 99.26 | 99.33 | 99.23 | 98.39 | 96.69 |
| 4.1 | Appearance | MR | MR | MR | MR | MR | MR | MR |
|  | pH | 4.13 | 4.21 | 4.27 | 4.20 | 4.22 | 4.11 | 4.38 |
|  | Assay % | 101.1 | 99.1 | 99.2 | 98.8 | 98.7 | 95.6 | 93.6 |
|  | Chromatographic purity (%) | 99.4 | 99.25 | 99.23 | 98.95 | 99.02 | 97.40 | 94.66 |
| 4.5 | Appearance | MR | MR | MR | MR | MR | MR | MR |
|  | pH | 4.51 | 4.56 | 4.66 | 4.56 | 4.59 | 4.55 | 4.70 |
|  | Assay % | 101.0 | 98.6 | 98.8 | 98.8 | 98.8 | 93.4 | 90.2 |
|  | Chromatographic purity (%) | 99.50 | 99.30 | 99.08 | 98.88 | 98.84 | 95.15 | 89.97 |

As seen from Table 2, vasopressin formulations in acetate buffer having pH 2.9, 3.3, 3.7, 4.1 and 4.5 were all stable by appearance and chromatographic testing for at least 3 months when stored at about 25° C./60% RH. The formulation having pH 2.5 was stable to at least the 4 week time point but at 3 months was beginning to show significant degradation; by the 6 month time point, this formulation failed all three of the stability tests. The pH measurements showed a greater than optimal variation of the solution having pH 3.3 at the 1 and 2 week time points, (+0.23 and +0.22 pH units, respectively). After 6 months of storage, every formulation demonstrated greater than optimal pH variation regardless of pH. Thus, none of the acetate formulations were stable following storage of 6 months at accelerated room temperature conditions.

Table 3 below sets forth the stability results of acetate formulations prepared as described above having pH 2.5, 2.9, 3.3, 3.7, 4.1 and 4.5. The formulations were stored at 30±2° C., 65±5% RH for 1 week, 2 weeks, 3 weeks, 4 weeks, 3 months and 6 months.

TABLE 3

Stability of vasopressin formulations in acetate buffer following extended storage of 30 ± 2° C., 65 ± 5% RH as a function of pH

| pH | Testing | $T_0$ | 1 wk | 2 wks | 3 wks | 4 wks | 3 mo | 6 mo |
|---|---|---|---|---|---|---|---|---|
| 2.5 | Appearance | MR | MR | MR | MR | MR | MR | MR |
|  | pH | 2.62 | 2.72 | 2.71 | 2.69 | 2.67 | 2.73 | 2.91 |
|  | Assay % | 101.3 | 98.3 | 97.8 | 97.2 | 96.1 | 85.3 | 76.4 |
|  | Chromatographic purity (%) | 98.83 | 97.67 | 96.67 | 95.49 | 94.34 | 84.74 | 76.82 |
| 2.9 | Appearance | MR | MR | MR | MR | MR | MR | MR |
|  | pH | 2.96 | 3.14 | 3.12 | 3.10 | 3.15 | 3.12 | 3.38 |
|  | Assay % | 101.5 | 99.1 | 98.6 | 99.1 | 98.4 | 92.7 | 87.9 |
|  | Chromatographic purity (%) | 99.25 | 98.83 | 98.25 | 97.82 | 97.32 | 93.83 | 89.50 |
| 3.3 | Appearance | MR | MR | MR | MR | MR | MR | MR |
|  | pH | 3.30 | 3.54 | 3.53 | 3.49 | 3.55 | 3.57 | 3.74 |
|  | Assay % | 101.1 | 99.4 | 97.9 | 99.6 | 99.4 | 94.9 | 91.7 |
|  | Chromatographic purity (%) | 99.39 | 99.27 | 98.87 | 98.74 | 98.56 | 96.89 | 94.20 |
| 3.7 | Appearance | MR | MR | MR | MR | MR | MR | MR |
|  | pH | 3.69 | 3.85 | 3.81 | 3.80 | 3.84 | 3.86 | 4.02 |
|  | Assay % | 101.4 | 98.8 | 99.5 | 100.2 | 99.9 | 95.0 | 92.5 |
|  | Chromatographic purity (%) | 99.57 | 99.43 | 99.31 | 99.00 | 98.86 | 97.22 | 94.54 |
| 4.1 | Appearance | MR | MR | MR | MR | MR | MR | MR |
|  | pH | 4.13 | 4.21 | 4.25 | 4.19 | 4.23 | 4.18 | 4.39 |
|  | Assay % | 101.1 | 99.1 | 99.1 | 99.9 | 99.6 | 94.0 | 88.4 |
|  | Chromatographic purity (%) | 99.40 | 99.31 | 99.08 | 98.85 | 98.50 | 95.04 | 90.30 |

TABLE 3-continued

Stability of vasopressin formulations in acetate buffer following extended storage of 30 ± 2° C., 65 ± 5% RH as a function of pH

| pH | Testing | $T_0$ | 1 wk | 2 wks | 3 wks | 4 wks | 3 mo | 6 mo |
|---|---|---|---|---|---|---|---|---|
| 4.5 | Appearance | MR | MR | MR | MR | MR | MR | MR |
|  | pH | 4.51 | 4.57 | 4.63 | 4.56 | 4.61 | 4.50 | 4.72 |
|  | Assay % | 101.0 | 94.3 | 90.4 | 86.1 | 83.5 | 55.0 | 79.9 |
|  | Chromatographic purity (%) | 99.50 | 96.22 | 92.99 | 86.93 | 83.52 | 57.10 | 80.97 |

As seen from Table 3, vasopressin formulations in acetate buffer having pH 2.9, 3.7, and 4.1 were stable by appearance, pH, and chromatographic testing for at least 3 months when stored at about 30° C./65% RH. The formulation having pH 2.5 was stable at least 4 weeks but by 3 months, had significant degradation of the peptide. The pH measurements showed a greater than optimal variation of the solution having pH 3.3 at the 1, 2 and 4 week time points, as well as at the 3 month testing. The acetate formulation of pH 4.5 was stable for only 2 weeks under about 30° C./65% RH storage conditions, after which point the formulation failed both chromatographic measurements. Following 6 months of storage at about 30° C., 65% RH, all of the acetate buffered formulations failed the pH stability test, with a pH variation of greater than 0.2 pH units. In addition, acetate formulations having pH 2.5, 2.9, 4.1 and 4.5 failed at least one of the chromatographic stability tests following 6 months of storage.

The stability of vasopressin formulations in acetate buffer was also determined for storage conditions of about 40° C./75% RH and about 50° C. (data not shown). At about 40° C./75% RH, the formulation having pH 2.5 was stable for only 2 weeks; at the 3 week time point, the formulation failed the test for relative chromatographic purity and failed both chromatography tests at 4 weeks. The formulation having pH 2.9 was stable by all testing methods up to 4 weeks but failed both of the 3 month chromatography tests. The pH 3.3 formulation demonstrated the same increased pH variation of greater than 0.2 pH units noted above for all testing points except the 3 month test. The solution was chromatographically stable for at least 4 weeks; at the 3 month testing point, the pH 3.3 formulation failed both chromatographic tests. The acetate-buffered formulations having pH 3.7 and 4.1 also demonstrated chromatographic stability of at least 4 weeks following storage at about 40° C./75% RH. Finally, the pH 4.5 formulation was stable for only 2 weeks, after which time the formulation failed both chromatographic tests. Following 6 months of storage at about 40° C./75% RH, none of the acetate buffered formulations passed any of the stability tests.

For the about 50° C. storage testing, the acetate-buffer formulation having pH 2.5 maintained stability by the pH measurement but failed both chromatography tests at the 2 week time point. The formulation having pH 2.9 failed pH stability even at the 1 week testing mark, but was stable by chromatographic assay and relative chromatographic purity for at least 3 weeks. The pH 3.3 formulation failed the pH stability assay at each of the time points tested, but demonstrated chromatographic stability for at least 4 weeks. Similarly, the pH 3.7 solution was stable by pH only at the 1 week testing point, but was stable by both chromatographic tests out to 3 weeks. Formulations having pH 4.1 were stable for only one week when stored at about 50° C., while the formulation having pH 4.5 was not stable at all (<1 week).

Example 2—Modeling Shelf-Life Prediction

Shelf-life prediction was modeled for the various pH formulations based on the stability data reported above. The predictive model applies the Arrhenius Equation first order reaction kinetics (Eq. 1).

$$k = Ae^{\frac{-Ea}{RT}} \quad \text{(Eq. 1)}$$

where k=rate constant
T=absolute temperature (K)
A=pre-exponential factor, a constant for each chemical reaction
$E_a$=activation energy for the reaction (same units as RT)
R=Universal gas constant Table 4 below shows the predicted shelf-life of vasopressin formulations in acetate buffer formulations based on the stability measurements and the modeling outlined above. Based on the model, it is expected that vasopressin formulations in acetate buffer with pH 3.3 can be stored in the refrigerator (5±3° C.) for up to about 117 months. Refrigerated storage improves to 132 months and 138 months for formulations having pH 3.7 and 4.1, respectively.

TABLE 4

Predicted stability (in months) of vasopressin formulations in acetate buffer at various pHs and storage temperatures

| Temp (° C.) | pH 2.5 | pH 2.9 | pH 3.3 | pH 3.7 | pH 4.1 | pH 4.5 |
|---|---|---|---|---|---|---|
| 5 | 22.4 | 67.7 | 189.3 | 141.6 | 155.1 | 71.5 |
| 25 | 3.4 | 8.8 | 16.8 | 13.4 | 8.8 | 4.3 |
| 30 | 2.2 | 5.5 | 9.6 | 7.8 | 4.5 | 2.3 |
| 40 | 1.0 | 2.3 | 3.3 | 2.8 | 1.3 | 0.7 |
| 50 | 0.5 | 1.0 | 1.2 | 1.1 | 0.4 | 0.2 |

The predicted stability for acetate-buffered vasopressin formulations under refrigerated (5±3° C.) conditions is highest for formulations having pH≥3.3. For example, the predicted storage life of acetate-buffered formulations stored under refrigerated conditions is up to 189 months, 141 months and 155 months for pH 3.3, 3.7 and 4.1, respectively. The predicted storage stability for formulations stored at 5° C. having pH less than 3.3 is significantly less, with formulations of pH 2.9 and 2.5 are each predicted to be stable only for up to 22 and 67 months, respectively.

At room temperature, the predicted most stable solution is that with pH 3.3, having a stability of up to 16 months. When the pH is decreased below 3.3, the predicted stability drops to less than 9 months when stored at room temperature. As shown in Table 4, there is virtually no predicted stability for any storage conditions regardless of pH for acetate buffered formulations stored at temperatures over 25° C., with the best possible conditions being 9 months of storage at 25° C. for a formulation having pH 3.3.

Example 3—Stability Determination for Vasopressin in Lactate Buffer Formulations This example demonstrates the stability of exemplary formulations comprising vasopressin acetate in lactate buffer. Vasopressin formulations were made to include 20 units/mL (37.74 μg/mL) vasopressin in about 10 mM sodium lactate buffer. The pH of the various formulations was adjusted to 2.9, 3.3, 3.7, 4.1 and 4.5 with 1N HCl and/or 1N NaOH. The formulations were stored in a 2 cc blow back, clear, Type I glass vials with 13 mm, 4432/50 Grey West (Teflon 2 coating) Westar Silicone stoppers. The filter membrane was a Millipore Durapore PVDF disk membrane with a 0.22 μm pore size and 47 mm diameter. Flush volumes were applied to compensate for peptide surface adsorptions. The fill volume was 1 mL. All vials were stored in upright positions under the storage conditions forth in the examples below.

Table 5 below sets forth the stability results of formulations prepared as set forth above having pH 2.5, 2.9, 3.3, 3.7, 4.1 and 4.5. The formulations were stored at 5±3° C. for 1 week, 2 weeks, 3 weeks, 4 weeks, 3 months and 6 months.

As seen from Table 5, all of the vasopressin formulations in lactate buffer stored at about 5° C. were stable by each of the appearance, pH and chromatographic tests for at least 6 months. Notably, the lactate buffered solutions demonstrate very little pH variability when stored at about 5° C. as indicated by all solutions having ≤0.2 pH unit variance at 6 months. After 6 months of refrigerated storage, all of the sample formulations retained greater than 96% of the initial concentration of vasopressin with less than 4% total degradation products based on the chromatographic assay. Likewise, the relative chromatographic purity for all forms was greater than 95%. For formulations having pH 2.9 or higher, the relative chromatographic purity was greater than 970 at 6 months.

The HPLC chromatograms were analyzed for the inclusion of impurities/degradation products in each of the formulations. The formulations demonstrate that regardless of the pH, no individual impurity or degradation product becomes present at about 1% or more after storage for 6 months at about 5° C. Total degradation products in the formulations remained at less than about 5% after storage for 6 months at about 5° C. for the formulation having pH 2.5 and less than about 3% for all of the other formulations. The results for individual degradants and total degradants as determined by the HPLC method set forth above show the formulations are stable following extended storage under these conditions.

Table 6 below sets forth the stability results of formulations prepared as described above having pH 2.5, 2.9, 3.3, 3.7, 4.1 and 4.5. The formulations were stored at 25±2° C., 60±5% RH for 1 week, 2 weeks, 3 weeks, 4 weeks, 3 months and 6 months.

TABLE 5

Stability of vasopressin formulations in lactate buffer following extended storage of 5 ± 3° C. as a function of pH

| pH | Testing | $T_0$ | 1 wk | 2 wks | 3 wks | 4 wks | 3 mo | 6 mo |
|---|---|---|---|---|---|---|---|---|
| 2.5 | Appearance | MR | MR | MR | MR | MR | MR | MR |
| | pH | 2.46 | 2.53 | 2.50 | 2.56 | 2.56 | 2.47 | 2.66 |
| | Assay % | 102.2 | 100.4 | 100.7 | 102.0 | 101.1 | 98.4 | 100.8 |
| | Chromatographic purity (%) | 96.71 | 96.84 | 96.74 | 96.82 | 96.56 | 96.17 | 95.81 |
| 2.9 | Appearance | MR | MR | MR | MR | MR | MR | MR |
| | pH | 2.90 | 2.99 | 2.97 | 3.02 | 3.02 | 2.96 | 3.04 |
| | Assay % | 101.1 | 99.1 | 99.5 | 100.7 | 100.1 | 97.7 | 99.3 |
| | Chromatographic purity (%) | 97.13 | 97.10 | 97.05 | 97.17 | 97.06 | 96.99 | 97.52 |
| 3.3 | Appearance | MR | MR | MR | MR | MR | MR | MR |
| | pH | 3.26 | 3.39 | 3.36 | 3.41 | 3.38 | 3.31 | 3.36 |
| | Assay % | 100.9 | 99.1 | 99.0 | 100.4 | 100.4 | 97.4 | 100.2 |
| | Chromatographic purity (%) | 97.11 | 96.98 | 97.04 | 97.10 | 97.23 | 97.14 | 97.93 |
| 3.7 | Appearance | MR | MR | MR | MR | MR | MR | MR |
| | pH | 3.71 | 3.79 | 3.82 | 3.80 | 3.81 | 3.67 | 3.53 |
| | Assay % | 100.6 | 97.2 | 98.5 | 100.2 | 99.9 | 98.5 | 100.7 |
| | Chromatographic purity (%) | 97.12 | 96.91 | 97.13 | 97.27 | 97.25 | 97.36 | 98.15 |
| 4.1 | Appearance | MR | MR | MR | MR | MR | MR | MR |
| | pH | 4.08 | 4.27 | 4.24 | 4.22 | 4.20 | 4.05 | 4.11 |
| | Assay % | 100.1 | 98.0 | 98.6 | 98.8 | 99.6 | 97.4 | 100.9 |
| | Chromatographic purity (%) | 97.19 | 97.13 | 97.37 | 97.32 | 97.31 | 97.40 | 98.32 |
| 4.5 | Appearance | MR | MR | MR | MR | MR | MR | MR |
| | pH | 4.48 | 4.65 | 4.65 | 4.63 | 4.61 | 4.44 | 4.39 |
| | Assay % | 98.9 | 97.5 | 97.9 | 99.1 | 98.1 | 96.4 | 99.3 |
| | Chromatographic purity (%) | 97.12 | 97.02 | 97.14 | 97.24 | 97.36 | 97.33 | 98.13 |

TABLE 6

Stability of vasopressin formulations in lactate buffer following extended storage of 25 ± 2° C., 60 ± 5% RH as a function of pH

| pH | Testing | $T_0$ | 1 wk | 2 wks | 3 wks | 4 wks | 3 mo | 6 mo |
|---|---|---|---|---|---|---|---|---|
| 2.5 | Appearance | MR | MR | MR | MR | MR | MR | MR |
| | pH | 2.46 | 2.53 | 2.52 | 2.55 | 2.56 | 2.57 | 2.66 |
| | Assay % | 102.2 | 99.4 | 98.8 | 98.8 | 94.7 | 88.2 | 81.6 |
| | Chromatographic purity (%) | 96.71 | 96.05 | 95.42 | 94.80 | 94.23 | 86.38 | 78.36 |
| 2.9 | Appearance | MR | MR | MR | MR | MR | MR | MR |
| | pH | 2.90 | 3.01 | 2.99 | 3.06 | 3.02 | 2.92 | 3.04 |
| | Assay % | 101.1 | 99.1 | 99.1 | 99.4 | 99.4 | 94.1 | 92.5 |
| | Chromatographic purity (%) | 97.13 | 97.13 | 97.21 | 97.11 | 97.05 | 95.08 | 92.68 |
| 3.3 | Appearance | MR | MR | MR | MR | MR | MR | MR |
| | pH | 3.26 | 3.38 | 3.38 | 3.39 | 3.41 | 3.33 | 3.44 |
| | Assay % | 100.9 | 99.1 | 98.6 | 99.9 | 99.0 | 95.4 | 95.3 |
| | Chromatographic purity (%) | 97.11 | 97.25 | 97.37 | 97.35 | 97.64 | 97.09 | 95.59 |
| 3.7 | Appearance | MR | MR | MR | MR | MR | MR | MR |
| | pH | 3.71 | 3.80 | 3.84 | 3.82 | 3.78 | 3.75 | 3.72 |
| | Assay % | 100.6 | 97.2 | 97.9 | 99.4 | 97.8 | 94.8 | 96.5 |
| | Chromatographic purity (%) | 97.12 | 97.27 | 97.40 | 97.60 | 97.42 | 97.65 | 96.39 |
| 4.1 | Appearance | MR | MR | MR | MR | MR | MR | MR |
| | pH | 4.08 | 4.24 | 4.22 | 4.19 | 4.16 | 4.12 | 3.96 |
| | Assay % | 100.1 | 97.5 | 97.6 | 98.3 | 97.8 | 94.2 | 95.5 |
| | Chromatographic purity (%) | 97.19 | 97.31 | 97.63 | 97.75 | 97.89 | 97.27 | 95.76 |
| 4.5 | Appearance | MR | MR | MR | MR | MR | MR | MR |
| | pH | 4.48 | 4.67 | 4.59 | 4.55 | 4.50 | 4.35 | 4.26 |
| | Assay % | 98.9 | 97.2 | 96.2 | 97.5 | 95.3 | 90.4 | 91.5 |
| | Chromatographic purity (%) | 97.12 | 97.32 | 97.50 | 97.45 | 97.52 | 95.37 | 92.73 |

As seen from Table 6, following storage at about 25° C., 60% RH, the vasopressin in lactate buffer formulation having pH 2.5 was stable for at least 4 weeks, but after 3 months of storage at 25° C./60% RH, the pH 2.5 formulation failed both chromatographic tests. The vasopressin formulations in lactate buffer having pH 2.9, 3.3, 3.7, 4.1 and 4.5 were stable by all measurements for at least 3 months when stored at about 25° C./60% RH. Further, the vasopressin formulations in lactate buffer having pH 2.9, 3.3, 3.7, and 4.1 were stable by all measurements for at least 6 months when stored at about 25° C./60% RH. After 6 months of storage at about 25° C./60% RH, the formulations having pH 3.3, 3.7 and 4.1 all retained at least 95% of the initial concentration of vasopressin. The relative chromatographic purity of these formulations was each at least 95%. The formulations having pH 2.9 and 4.5 both retained greater than 90% of the initial concentration of vasopressin and had relative chromatographic purities of greater than 92%. Unlike the acetate buffered formulations, there was minimal pH variability in the formulations stored under these conditions, although at the 6 month storage test point, the pH 4.5 formulation was outside the optimal pH variability of ≤0.2 pH units.

The HPLC chromatograms were analyzed for the inclusion of impurities/degradation products in each of the formulations. The formulations that were stable at the 3 month time point (pH 2.9, 3.3, 3.7, 4.1 and 4.5) demonstrated that no individual impurity or degradation product became present in an amount greater than about 1% after storage for 3 months at about 25° C./60% RH. At 6 months, the formulations having pH 2.9, 3.3, 3.7 and 4.1 had no single degradant present in an amount of greater than about 3%. For the formulations having pH 2.9 or greater, the total degradants in the formulations remained at levels less than about 9% under the tested storage conditions. For the formulations having pH 3.3, 3.7 and 4.1, the total degradation products were less than about 5% after 6 months of 25° C./60% RH storage. The results for individual degradants and total degradants as determined by HPLC show the formulations having pH 2.9, 3.3, 3.7, 4.1 and 4.5 are stable for extended 25° C./60% RH storage.

Table 7 below sets forth the stability results of formulations prepared as described above having pH 2.5, 2.9, 3.3, 3.7, 4.1 and 4.5. The formulations were stored at 30±2° C., 65±5% RH for 1 week, 2 weeks, 3 weeks, 4 weeks, 3 months and 6 months.

TABLE 7

Stability of vasopressin formulations in lactate buffer following extended storage of 30 ± 2° C., 65 ± 5% RH as a function of pH

| pH | Testing | $T_0$ | 1 wk | 2 wks | 3 wks | 4 wks | 3 mo | 6 mo |
|---|---|---|---|---|---|---|---|---|
| 2.5 | Appearance | MR | MR | MR | MR | MR | MR | MR |
| | pH | 2.46 | 2.54 | 2.52 | 2.57 | 2.59 | 2.61 | 2.70 |
| | Assay % | 102.2 | 98.8 | 96.7 | 97.5 | 96.8 | 83.2 | 71.6 |
| | Chromatographic purity (%) | 96.71 | 95.90 | 94.83 | 93.33 | 92.29 | 80.66 | 69.07 |
| 2.9 | Appearance | MR | MR | MR | MR | MR | MR | MR |
| | pH | 2.90 | 3.02 | 3.00 | 3.07 | 3.06 | 3.07 | 3.19 |
| | Assay % | 101.1 | 98.3 | 98.6 | 99.1 | 99.2 | 92.6 | 88.0 |
| | Chromatographic purity (%) | 97.13 | 97.18 | 97.16 | 96.87 | 96.84 | 93.21 | 88.93 |
| 3.3 | Appearance | MR | MR | MR | MR | MR | MR | MR |
| | pH | 3.26 | 3.37 | 3.38 | 3.44 | 3.38 | 3.37 | 3.42 |

TABLE 7-continued

Stability of vasopressin formulations in lactate buffer following extended storage of 30 ± 2° C., 65 ± 5% RH as a function of pH

| pH | Testing | $T_0$ | 1 wk | 2 wks | 3 wks | 4 wks | 3 mo | 6 mo |
|---|---|---|---|---|---|---|---|---|
| | Assay % | 100.9 | 98.8 | 98.4 | 99.6 | 99.5 | 94.0 | 93.5 |
| | Chromatographic purity (%) | 97.11 | 97.28 | 97.54 | 97.50 | 97.66 | 95.95 | 93.28 |
| 3.7 | Appearance | MR | MR | MR | MR | MR | MR | MR |
| | pH | 3.71 | 3.79 | 3.78 | 3.82 | 3.79 | 3.69 | 3.79 |
| | Assay % | 100.6 | 98.0 | 98.0 | 98.3 | 99.2 | 93.6 | 92.7 |
| | Chromatographic purity (%) | 97.12 | 97.46 | 97.73 | 97.75 | 98.00 | 96.70 | 94.86 |
| 4.1 | Appearance | MR | MR | MR | MR | MR | MR | MR |
| | pH | 4.08 | 4.25 | 4.14 | 4.18 | 4.11 | 4.03 | 4.01 |
| | Assay % | 100.1 | 97.2 | 96.9 | 97.8 | 98.0 | 93.7 | 90.8 |
| | Chromatographic purity (%) | 97.19 | 97.53 | 97.79 | 97.75 | 97.80 | 95.73 | 92.28 |
| 4.5 | Appearance | MR | MR | MR | MR | MR | MR | MR |
| | pH | 4.48 | 4.63 | 4.56 | 4.54 | 4.45 | 4.33 | 4.27 |
| | Assay % | 98.9 | 96.4 | 95.6 | 94.3 | 95.4 | 88.4 | 49.6 |
| | Chromatographic purity (%) | 97.12 | 97.27 | 97.25 | 97.18 | 96.80 | 92.89 | 51.88 |

As seen from Table 7, vasopressin formulations in lactate buffer having pH 2.9 were stable for at least 3 months when stored at about 30° C./65% RH. The formulation having pH 2.9 retained greater than 92% of the initial vasopressin concentration after 3 months. After 6 months of storage, the pH 2.9 formulation failed all stability tests. Formulations in lactate buffer having pH 3.3, 3.7, and 4.1 were stable by all testing methods for at least 6 months when stored at about 30° C./65% RH. Formulations having pH 3.3, 3.7 and 4.1 each retained at least 90% of the initial vasopressin concentration following storage. Each of the formulations having pH 3.3, 3.7 and 4.1 demonstrated a relative chromatographic purity of greater than 92% under the tested storage conditions. The formulations with the highest and lowest pH, 4.5 and 2.5, were stable under these storage conditions for at least 4 weeks, but failed the chromatographic stability assay at 3 months. None of the formulations showed any significant pH variability over the first 3 months of testing. After 6 months of storage, the formulations having pH 2.5, 2.9 and 4.5 were outside the desired range.

The HPLC chromatograms were analyzed for the inclusion of impurities/degradation products in each of the stable formulations. The formulation having pH 3.3 demonstrated that no individual degradation product becomes present in an amount greater than about 2.4% after storage for 6 months at about 30° C./65% RH, total degradants in the formulation remained at less than about 7% after storage for 3 months. The formulation having pH 3.7 demonstrated total degradants of less than 6% and no individual degradant present in an amount of more than 1.5% following storage of 6 months under the stated conditions. For the formulation at pH 2.9, no single degradant was present at an amount of greater than about 5% following 6 months of storage.

Table 8 below sets forth the stability results of formulations prepared as described above having pH 2.5, 2.9, 3.3, 3.7, 4.1 and 4.5. The formulations were stored at 40±2° C., 75±5% RH for 1 week, 2 weeks, 3 weeks, 4 weeks, 3 months and 6 months.

TABLE 8

Stability of vasopressin formulations in lactate buffer following extended storage of 40 ± 2° C., 75 ± 5% RH as a function of pH

| pH | Testing | $T_0$ | 1 wk | 2 wks | 3 wks | 4 wks | 3 mo | 6 mo |
|---|---|---|---|---|---|---|---|---|
| 2.5 | Appearance | MR | MR | MR | MR | MR | MR | MR |
| | pH | 2.46 | 2.55 | 2.55 | 2.59 | 2.59 | 2.63 | 3.15 |
| | Assay % | 102.2 | 96.4 | 92.1 | 89.6 | 86.1 | 59.9 | 72.2 |
| | Chromatographic purity (%) | 96.71 | 93.63 | 89.72 | 85.51 | 82.06 | 57.25 | 72.71 |
| 2.9 | Appearance | MR | MR | MR | MR | MR | MR | MR |
| | pH | 2.90 | 3.04 | 3.07 | 3.10 | 3.10 | 3.10 | 3.15 |
| | Assay % | 101.1 | 97.0 | 96.1 | 95.4 | 94.8 | 83.3 | 72.2 |
| | Chromatographic purity (%) | 97.13 | 96.36 | 95.97 | 94.75 | 93.72 | 83.69 | 72.71 |
| 3.3 | Appearance | MR | MR | MR | MR | MR | MR | MR |
| | pH | 3.26 | 3.39 | 3.44 | 3.42 | 3.40 | 3.45 | 3.48 |
| | Assay % | 100.9 | 97.8 | 95.0 | 97.0 | 96.4 | 86.3 | 78.6 |
| | Chromatographic purity (%) | 97.11 | 97.47 | 96.91 | 96.41 | 95.98 | 88.32 | 79.97 |
| 3.7 | Appearance | MR | MR | MR | MR | MR | MR | MR |
| | pH | 3.71 | 3.88 | 3.81 | 3.80 | 3.80 | 3.66 | 3.76 |
| | Assay % | 100.6 | 97.0 | 96.1 | 94.9 | 94.4 | 84.7 | 74.5 |
| | Chromatographic purity (%) | 97.12 | 97.59 | 97.54 | 96.44 | 95.77 | 87.01 | 77.75 |
| 4.1 | Appearance | MR | MR | MR | MR | MR | MR | MR |
| | pH | 4.08 | 4.17 | 4.16 | 4.09 | 4.07 | 4.06 | 4.06 |
| | Assay % | 100.1 | 95.9 | 94.3 | 92.7 | 91.4 | 77.2 | 65.3 |
| | Chromatographic purity (%) | 97.19 | 97.46 | 96.50 | 94.54 | 93.63 | 81.16 | 67.10 |
| 4.5 | Appearance | MR | MR | MR | MR | MR | MR | MR |
| | pH | 4.48 | 4.51 | 4.38 | 4.35 | 4.32 | 4.29 | 4.27 |
| | Assay % | 98.9 | 87.2 | 78.4 | 73.1 | 67.7 | 37.1 | 49.6 |
| | Chromatographic purity (%) | 97.12 | 91.54 | 82.90 | 75.45 | 71.03 | 39.75 | 51.88 |

As seen from Table 8 above, vasopressin formulations in lactate buffer having pH 2.9, 3.3, 3.7, and 4.1 were stable (appearance, pH and chromatographic assays) for at least 4 weeks when stored at about 40° C./75% RH, with each formulation retaining greater than 91% of the initial vasopressin concentration and having less than 9% total degradants. The vasopressin in lactate buffer formulations having a pH of 2.5 and 4.5 were stable for only one week when stored at about 40° C./75% RH before the formulations failed the chromatographic purity test for stability.

Table 9 below sets forth the stability results of formulations prepared as described above having pH 2.5, 2.9, 3.3, 3.7, 4.1 and 4.5. The formulations were stored at 50±2° C. for 1 week, 2 weeks, 3 weeks, 4 weeks, and 3 months.

Example 4—Modeling Shelf-Life Prediction

A shelf-life prediction was modeled for the various pH formulations in lactate buffer based on the stability data reported in Example 3 above. The modeling was carried out as described in Example 2.

Table 10 below shows the predicted shelf-life of vasopressin in lactate buffer formulations based on the stability measurements (chromatographic purity) and the modeling outlined above. Based on the predictions, it is expected that vasopressin formulations in lactate buffer with pH 3.3-3.7 can be stored in the refrigerator (5±3° C.) for over 300 months. Even at pH 2.9, the formulation is expected to be refrigerated stable for over 8 years (98 months).

TABLE 9

Stability of vasopressin formulations in lactate buffer following extended storage of 50 ± 2° C. as a function of pH

| pH | Testing | $T_0$ | 1 wk | 2 wks | 3 wks | 4 wks | 3 mo |
|---|---|---|---|---|---|---|---|
| 2.5 | Appearance | MR | MR | MR | MR | MR | MR |
| | pH | 2.46 | 2.57 | 2.56 | 2.59 | 2.61 | 2.56 |
| | Assay % | 102.2 | 92.5 | 85.0 | 79.0 | 74.4 | 42.3 |
| | Chromatographic purity (%) | 96.71 | 90.20 | 82.25 | 75.86 | 70.38 | 40.79 |
| 2.9 | Appearance | MR | MR | MR | MR | MR | MR |
| | pH | 2.90 | 3.06 | 3.07 | 3.12 | 3.13 | 3.07 |
| | Assay % | 101.1 | 95.9 | 93.2 | 90.9 | 89.0 | 70.4 |
| | Chromatographic purity (%) | 97.13 | 96.11 | 93.51 | 90.82 | 88.10 | 70.30 |
| 3.3 | Appearance | MR | MR | MR | MR | MR | MR |
| | pH | 3.26 | 3.40 | 3.47 | 3.46 | 3.44 | 3.47 |
| | Assay % | 100.9 | 96.7 | 94.2 | 91.4 | 91.2 | 74.4 |
| | Chromatographic purity (%) | 97.11 | 97.16 | 95.58 | 93.45 | 91.10 | 75.57 |
| 3.7 | Appearance | MR | MR | MR | MR | MR | MR |
| | pH | 3.71 | 3.80 | 3.83 | 3.82 | 3.79 | 3.67 |
| | Assay % | 100.6 | 94.6 | 92.3 | 90.4 | 89.2 | 70.9 |
| | Chromatographic purity (%) | 97.12 | 96.90 | 95.16 | 92.32 | 90.55 | 74.49 |
| 4.1 | Appearance | MR | MR | MR | MR | MR | MR |
| | pH | 4.08 | 4.18 | 4.14 | 4.11 | 4.07 | 4.00 |
| | Assay % | 100.1 | 92.2 | 86.9 | 84.3 | 80.3 | 53.4 |
| | Chromatographic purity (%) | 97.19 | 95.58 | 91.93 | 86.51 | 81.85 | 56.34 |
| 4.5 | Appearance | MR | MR | MR | MR | MR | MR |
| | pH | 4.48 | 4.51 | 4.38 | 4.35 | 4.32 | 4.29 |
| | Assay % | 98.9 | 87.2 | 78.4 | 73.1 | 67.7 | 37.1 |
| | Chromatographic purity (%) | 97.12 | 91.57 | 82.90 | 75.45 | 71.03 | 39.75 |

Table 9 shows that vasopressin formulations in lactate buffer stored at about 50° C. having pH 3.3 demonstrated the best stability by all four tests out to 4 weeks. The formulations having pH 2.9 and 3.7 were stable for at least 3 weeks when stored at about 50° C. but failed the chromatographic stability test(s) when monitored at 4 weeks. The vasopressin in lactate buffer formulation having a pH of 4.1 was stable by all three tests for 2 weeks and the formulations at pH 2.5 and 4.5 were stable for only one week when stored at about 50° C. No formulation was stable at the 6 month testing point.

It is noteworthy that the lactate buffered formulations demonstrated much better pH stability over all pH and storage conditions than did the acetate buffered formulations tested in Example 1. For the lactate formulations, the only pH variation following storage that was greater than ±0.2 pH units before the formulation failed the chromatographic testing was in the pH 2.9 and 3.3 formulations and only when stored at about 50° C. That is, overall the lactate buffered vasopressin formulations demonstrate much greater pH stability than do the acetate buffered formulations for long-term stability.

TABLE 10

Predicted stability (in months) of vasopressin formulations in lactate buffer at various pHs and storage temperatures

| Temp (° C.) | pH 2.5 | pH 2.9 | pH 3.3 | pH 3.7 | pH 4.1 | pH 4.5 |
|---|---|---|---|---|---|---|
| 5 | 18.5 | 98.6 | 327.0 | 359.6 | 331.3 | 163.0 |
| 25 | 2.7 | 10.6 | 22.8 | 22.9 | 15.5 | 8.3 |
| 30 | 1.7 | 6.4 | 12.4 | 12.2 | 7.7 | 4.2 |
| 40 | 0.7 | 2.4 | 3.9 | 3.6 | 2.0 | 1.1 |
| 50 | 0.3 | 1.0 | 1.3 | 1.2 | 0.6 | 0.3 |

The vasopressin in lactate formulations of the present disclosure show particular improvement compared to the acetate-buffered formulations in the predicted room temperature (~25° C.) storage conditions. As seen in Table 10, the model predicts that vasopressin in lactate buffer will be stable for at least 22 months when formulated at pH 3.3. Based on the data, at pH 3.7, vasopressin in lactate buffer formulations are expected to be stable for about 23 months.

These predictions were confirmed in an 18 month stability test. As seen in Table 11 below, formulations having pH 2.9 that were stored at 5° C. for 18 months were stable by both the pH assay and the chromatographic purity assay following the storage period. As expected, formulations having pH 2.9 that were stored at about 25° C./60% RH for 18 months failed both the pH assay and the chromatographic purity assay. Likewise, vasopressin formulations having pH 3.3 were stable following 18 months in storage both at 5° C. and at 25° C./60% RH.

TABLE 11

Stability of vasopressin formulations in lactate buffer following 18 month storage

| pH | Testing | 5° C. | 25° C. |
|---|---|---|---|
| 2.9 | Appearance | MR | MR |
|  | pH | 2.94 | 3.2 |
|  | Chromatographic purity (%) | 102.7 | 83.8 |
| 3.3 | Appearance | MR | MR |
|  | pH | 3.30 | 3.31 |
|  | Chromatographic purity (%) | 103.0 | 91.9 |

Example 5—Stability Determination for High Concentration Vasopressin in Lactate Buffer Formulations This example demonstrates the stability of exemplary formulations comprising a high concentration of vasopressin acetate in lactate buffer. Vasopressin formulations were made to include 100 units/mL (188.7 μg/mL) in about 10 mM sodium lactate buffer. The pH of the various formulations was adjusted to 2.5, 2.9, 3.3, 3.7, 4.1 and 4.5 with 1N HCl and/or 1N NaOH. The formulations were stored as described in Examples 1 and 3 above.

Table 12 below sets forth the stability results of formulations prepared as set forth above having pH 2.5, 2.9, 3.3, 3.7, 4.1 and 4.5. The formulations were stored at 5±3° C. for 1 week, 2 weeks, 3 weeks, 4 weeks and 3 months.

Table 12 demonstrates that vasopressin formulations in lactate buffer having higher vasopressin concentrations (100 units/mL) are stable for greater than 3 months regardless of pH when stored in refrigerated (about 5° C.) conditions. All formulations were stable by all three tests for the 3 month storage period. In particular, after 3 months of refrigerated storage, all of the sample formulations retained at least 97% of the initial concentration of vasopressin with less than 3% total degradants. Notably, the high vasopressin concentration in lactate buffer solutions demonstrate very little pH variability when stored at about 5° C.

The HPLC chromatograms were analyzed for the inclusion of degradants in each of the formulations. The formulations demonstrate that no individual degradation product becomes present at levels greater than about 0.4% after storage for 3 months at about 5° C. Total degradants in the formulations remained at levels less than about 3%, and in some cases, less than about 1% after storage for 3 months at about 5° C. The results for individual degradants and total degradants as determined by HPLC show the formulations are stable following storage at about 5° C. at all pH values tested.

Table 13 below sets forth the stability results of formulations prepared as set forth above having pH 2.5, 2.9, 3.3, 3.7, 4.1 and 4.5. The formulations were stored at 25° C./60±5% RH for 1 week, 2 weeks, 3 weeks, 4 weeks and 3 months.

TABLE 12

Stability of high concentration vasopressin formulations in lactate buffer following extended storage of 5 ± 3° C. as a function of pH

| pH | Testing | $T_0$ | 1 wk | 2 wks | 3 wks | 4 wks | 3 mo |
|---|---|---|---|---|---|---|---|
| 2.5 | Appearance | MR | MR | MR | MR | MR | MR |
|  | pH | 2.51 | 2.57 | 2.55 | 2.59 | 2.60 | 2.51 |
|  | Assay % | 102.2 | 100.8 | 101.2 | 102.4 | 100.3 | 99.0 |
|  | Chromatographic purity (%) | 98.39 | 98.37 | 98.18 | 98.29 | 97.95 | 97.47 |
| 2.9 | Appearance | MR | MR | MR | MR | MR | MR |
|  | pH | 2.89 | 2.98 | 2.96 | 3.02 | 3.02 | 3.01 |
|  | Assay % | 102.5 | 100.9 | 101.7 | 102.6 | 100.3 | 99.5 |
|  | Chromatographic purity (%) | 98.79 | 98.71 | 98.70 | 98.83 | 98.69 | 98.54 |
| 3.3 | Appearance | MR | MR | MR | MR | MR | MR |
|  | pH | 3.32 | 3.40 | 3.46 | 3.46 | 3.42 | 3.25 |
|  | Assay % | 102.8 | 101.2 | 101.9 | 102.9 | 101.0 | 100.1 |
|  | Chromatographic purity (%) | 98.90 | 99.04 | 98.97 | 99.00 | 98.79 | 98.98 |
| 3.7 | Appearance | MR | MR | MR | MR | MR | MR |
|  | pH | 3.75 | 3.80 | 3.84 | 3.89 | 3.83 | 3.67 |
|  | Assay % | 102.6 | 101.2 | 101.7 | 102.6 | 100.0 | 98.8 |
|  | Chromatographic purity (%) | 98.93 | 98.98 | 99.01 | 99.21 | 99.01 | 99.14 |
| 4.1 | Appearance | MR | MR | MR | MR | MR | MR |
|  | pH | 4.11 | 4.26 | 4.20 | 4.26 | 4.19 | 4.01 |
|  | Assay % | 102.8 | 101.6 | 102.1 | 102.7 | 100.9 | 100.4 |
|  | Chromatographic purity (%) | 98.97 | 99.04 | 99.01 | 99.14 | 98.99 | 99.16 |
| 4.5 | Appearance | MR | MR | MR | MR | MR | MR |
|  | pH | 4.55 | 4.70 | 4.61 | 4.71 | 4.66 | 4.42 |
|  | Assay % | 102.3 | 100.5 | 101.4 | 102.0 | 100.3 | 99.2 |
|  | Chromatographic purity (%) | 98.95 | 99.02 | 99.00 | 99.08 | 99.04 | 99.01 |

TABLE 13

Stability of high concentration vasopressin formulations in lactate buffer following extended storage of 25° C./60 ± 5% RH as a function of pH

| pH | Testing | $T_0$ | 1 wk | 2 wks | 3 wks | 4 wks | 3 mo |
|---|---|---|---|---|---|---|---|
| 2.5 | Appearance | MR | MR | MR | MR | MR | MR |
| | pH | 2.51 | 2.57 | 2.56 | 2.62 | 2.60 | 2.51 |
| | Assay % | 102.2 | 100.2 | 99.9 | 99.4 | 97.1 | 89.4 |
| | Chromatographic purity (%) | 98.39 | 97.67 | 96.81 | 96.03 | 95.13 | 88.03 |
| 2.9 | Appearance | MR | MR | MR | MR | MR | MR |
| | pH | 2.89 | 2.97 | 2.97 | 3.05 | 3.04 | 3.05 |
| | Assay % | 102.5 | 100.6 | 101.1 | 101.9 | 99.5 | 96.0 |
| | Chromatographic purity (%) | 98.79 | 98.53 | 98.35 | 98.10 | 97.66 | 95.34 |
| 3.3 | Appearance | MR | MR | MR | MR | MR | MR |
| | pH | 3.32 | 3.41 | 3.40 | 3.49 | 3.44 | 3.36 |
| | Assay % | 102.8 | 101.2 | 101.8 | 102.2 | 100.3 | 97.8 |
| | Chromatographic purity (%) | 98.90 | 98.94 | 98.77 | 98.72 | 98.52 | 97.53 |
| 3.7 | Appearance | MR | MR | MR | MR | MR | MR |
| | pH | 3.75 | 3.79 | 3.79 | 3.89 | 3.83 | 3.63 |
| | Assay % | 102.6 | 100.7 | 101.4 | 101.6 | 99.8 | 97.5 |
| | Chromatographic purity (%) | 98.93 | 99.02 | 98.95 | 98.98 | 98.84 | 97.82 |
| 4.1 | Appearance | MR | MR | MR | MR | MR | MR |
| | pH | 4.11 | 4.18 | 4.19 | 4.22 | 4.15 | 4.05 |
| | Assay % | 102.8 | 101.3 | 101.3 | 101.7 | 100.0 | 95.8 |
| | Chromatographic purity (%) | 98.97 | 98.96 | 98.96 | 98.81 | 98.41 | 96.66 |
| 4.5 | Appearance | MR | MR | MR | MR | MR | MR |
| | pH | 4.55 | 4.69 | 4.63 | 4.64 | 4.57 | 4.37 |
| | Assay % | 102.3 | 100.3 | 100.6 | 100.1 | 98.6 | 92.9 |
| | Chromatographic purity (%) | 98.95 | 98.80 | 98.37 | 98.20 | 97.39 | 93.16 |

Table 13 demonstrates that vasopressin formulations in lactate buffer having higher vasopressin concentrations (100 units/mL) are stable for greater than 3 months for all pH≥2.9 when stored at about 25° C./60% RH; all of these formulations were stable by all three tests for the 3 month storage period. After 3 months of storage at about 25° C./60% RH, the formulations having pH 3.3 and 3.7 both retained greater than 97% of the initial concentration of vasopressin based on the chromatographic assay. The formulations having pH 2.9 and 4.1 both retained greater than 95% of the initial concentration of vasopressin. The formulation having pH 4.5 retained greater than 92% of the initial vasopressin concentration. The relative chromatographic purities of all formulations were substantially similar. The formulation having pH 2.5 was stable for more than 4 weeks under the about 25° C./60% RH storage conditions but failed both chromatographic tests at the 3 month testing period. Unlike the acetate buffered formulations, there was minimal pH variability in the formulations stored at about 25° C./60% RH.

The HPLC chromatograms for the stable formulations were analyzed for the inclusion of degradants in each of the formulations. The formulations with pH 3.3, 3.7 and 4.1 demonstrate that no individual degradation product becomes present in levels greater than about 1.2% after storage for 3 months at about 25° C./60% RH. Total degradants in the formulations having pH 3.3 and 3.7 remained at less than about 3% after storage for 3 months; for the pH 4.1 formulation, total degradants were less than about 4% under the tested storage conditions. The results for individual degradants and total degradants as determined by HPLC show the formulation is stable for at least 3 months at about 25° C./60% RH.

Table 14 below sets forth the stability results of formulations prepared as set forth above having pH 2.5, 2.9, 3.3, 3.7, 4.1 and 4.5. The formulations were stored at 30±2° C./65±5% RH for 1 week, 2 weeks, 3 weeks, 4 weeks and 3 months.

TABLE 14

Stability of high concentration vasopressin formulations in lactate buffer following extended storage of 30 ± 2° C./65 ± 5% RH as a function of pH

| pH | Testing | $T_0$ | 1 wk | 2 wks | 3 wks | 4 wks | 3 mo |
|---|---|---|---|---|---|---|---|
| 2.5 | Appearance | MR | MR | MR | MR | MR | MR |
| | pH | 2.51 | 2.56 | 2.57 | 2.57 | 2.64 | 2.60 |
| | Assay % | 102.2 | 100.0 | 99.1 | 98.5 | 95.8 | 83.9 |
| | Chromatographic purity (%) | 98.39 | 97.21 | 95.70 | 94.39 | 93.21 | 82.74 |
| 2.9 | Appearance | MR | MR | MR | MR | MR | MR |
| | pH | 2.89 | 3.01 | 2.99 | 3.01 | 3.06 | 3.12 |
| | Assay % | 102.5 | 100.6 | 100.7 | 101.3 | 98.9 | 94.2 |
| | Chromatographic purity (%) | 98.79 | 98.41 | 97.86 | 97.58 | 97.11 | 93.34 |
| 3.3 | Appearance | MR | MR | MR | MR | MR | MR |
| | pH | 3.32 | 3.39 | 3.42 | 3.41 | 3.43 | 3.40 |
| | Assay % | 102.8 | 101.0 | 101.3 | 103.6 | 99.2 | 96.8 |
| | Chromatographic purity (%) | 98.90 | 98.84 | 98.58 | 98.51 | 98.37 | 96.51 |
| 3.7 | Appearance | MR | MR | MR | MR | MR | MR |
| | pH | 3.75 | 3.79 | 3.83 | 3.80 | 3.80 | 3.76 |
| | Assay % | 102.6 | 100.3 | 100.8 | 103.1 | 99.4 | 96.1 |
| | Chromatographic purity (%) | 98.93 | 98.98 | 98.84 | 98.62 | 98.56 | 96.35 |

TABLE 14-continued

Stability of high concentration vasopressin formulations in lactate buffer
following extended storage of 30 ± 2° C./65 ± 5% RH as a function of pH

| pH | Testing | $T_0$ | 1 wk | 2 wks | 3 wks | 4 wks | 3 mo |
|---|---|---|---|---|---|---|---|
| 4.1 | Appearance | MR | MR | MR | MR | MR | MR |
| | pH | 4.11 | 4.23 | 4.14 | 4.11 | 4.12 | 4.06 |
| | Assay % | 102.8 | 100.6 | 101.2 | 102.8 | 98.8 | 94.7 |
| | Chromatographic purity (%) | 98.97 | 98.82 | 98.52 | 98.07 | 97.67 | 94.47 |
| 4.5 | Appearance | MR | MR | MR | MR | MR | MR |
| | pH | 4.55 | 4.63 | 4.58 | 4.52 | 4.52 | 4.34 |
| | Assay % | 102.3 | 98.9 | 99.4 | 99.4 | 95.6 | 87.4 |
| | Chromatographic purity (%) | 98.95 | 98.39 | 97.39 | 95.96 | 95.42 | 88.00 |

As seen from Table 14, the formulations following storage at about 30° C./65% RH demonstrate high pH stability for pH≥3.3 over all of the conditions tested. The formulations having pH 2.9, 3.3, 3.7 and 4.1 were stable over the 3 month storage period according to all three stability tests. In the examples having pH 3.3 and 3.7, more than 96% of the initial vasopressin concentration was retained following 3 months of storage. In other words, the formulations having pH 3.3 and 3.7 contained less than 4% total degradants following 3 months at about 30° C./65% RH. The formulations having pH 2.9 and 4.1 each retained at least 94% of the total vasopressin concentration, with less than 6% total degradants after 3 months. The formulations having pH 2.5 and 4.5 were stable for at least 4 weeks when stored at about 30° C./65% RH but both failed the chromatographic testing at the 3 month time point.

The HPLC chromatograms were analyzed for the inclusion of degradants in each of the stable formulations. The chromatographic purity demonstrated that for the formulations having pH 3.3 and 3.7, no individual degradant becomes present at an amount greater than about 1.2% after storage for 3 months at about 30° C./65% RH. For the formulations having pH 2.9 and 4.1, no individual degradant is present in an amount greater than about 3% following 3 months of storage as indicated.

Table 15 below sets forth the stability results of formulations prepared as set forth above having pH 2.5, 2.9, 3.3, 3.7, 4.1 and 4.5. The formulations were stored at 40±2° C./75±5% RH for 1 week, 2 weeks, 3 weeks, 4 weeks and 3 months.

TABLE 15

Stability of high concentration vasopressin formulations in lactate buffer
following extended storage of 40 ± 2° C./75 ± 5% RH as a function of pH

| pH | Testing | $T_0$ | 1 wk | 2 wks | 3 wks | 4 wks | 3 mo |
|---|---|---|---|---|---|---|---|
| 2.5 | Appearance | MR | MR | MR | MR | MR | MR |
| | pH | 2.51 | 2.57 | 2.58 | 2.66 | 2.65 | 2.61 |
| | Assay % | 102.2 | 96.3 | 94.1 | 90.4 | 86.5 | 62.5 |
| | Chromatographic purity (%) | 98.39 | 94.65 | 91.34 | 86.86 | 83.92 | 61.30 |
| 2.9 | Appearance | MR | MR | MR | MR | MR | MR |
| | pH | 2.89 | 3.01 | 3.02 | 3.13 | 3.11 | 3.05 |
| | Assay % | 102.5 | 99.2 | 98.4 | 97.8 | 95.3 | 83.4 |
| | Chromatographic purity (%) | 98.79 | 97.59 | 96.26 | 94.86 | 93.55 | 83.32 |
| 3.3 | Appearance | MR | MR | MR | MR | MR | MR |
| | pH | 3.32 | 3.44 | 3.43 | 3.52 | 3.45 | 3.45 |
| | Assay % | 102.8 | 99.7 | 99.8 | 99.9 | 97.2 | 88.3 |
| | Chromatographic purity (%) | 98.90 | 98.52 | 97.76 | 96.87 | 96.09 | 87.98 |
| 3.7 | Appearance | MR | MR | MR | MR | MR | MR |
| | pH | 3.75 | 3.81 | 3.81 | 3.85 | 3.81 | 3.84 |
| | Assay % | 102.6 | 99.1 | 99.0 | 98.3 | 95.7 | 84.2 |
| | Chromatographic purity (%) | 98.93 | 98.47 | 97.48 | 96.34 | 94.97 | 85.07 |
| 4.1 | Appearance | MR | MR | MR | MR | MR | MR |
| | pH | 4.11 | 4.22 | 4.13 | 4.16 | 4.09 | 4.02 |
| | Assay % | 102.8 | 98.9 | 97.6 | 95.9 | 92.4 | 76.7 |
| | Chromatographic purity (%) | 98.97 | 97.71 | 95.59 | 93.18 | 90.94 | 77.00 |
| 4.5 | Appearance | MR | MR | MR | MR | MR | MR |
| | pH | 4.55 | 4.59 | 4.46 | 4.51 | 4.41 | 4.41 |
| | Assay % | 102.3 | 94.9 | 91.6 | 88.0 | 82.3 | 60.8 |
| | Chromatographic purity (%) | 98.95 | 94.73 | 89.68 | 85.45 | 81.64 | 61.65 |

Table 15 shows the measured stability of high concentration (100 units/mL) vasopressin formulations in lactate buffer at various pH following storage at about 40° C./75% RH. As with the other storage conditions studied, all of the formulations demonstrate high pH stability regardless of pH. However, according to the chromatographic stability tests, these formulations were less stable following storage at about 40° C./75% RH, with no formulation showing chromatographic stability at the 3 month testing point. The formulations having pH 2.9, 3.3, 3.7 and 4.1 were stable at least 4 weeks of storage according to all three stability tests. The pH 2.5 formulation was stable for at least 2 weeks under the tested storage conditions, while the formulation having pH 4.5 was stable for only 1 week when stored at about 40° C./75% RH.

Table 16 below sets forth the stability results of formulations prepared as set forth above having pH 2.5, 2.9, 3.3, 3.7, 4.1 and 4.5. The formulations were stored at 50±2° C. for 1 week, 2 weeks, 3 weeks, 4 weeks and 3 months.

TABLE 16

Stability of high concentration vasopressin formulations in lactate buffer following extended storage of 50 ± 2° C. as a function of pH

| pH | Testing | $T_0$ | 1 wk | 2 wks | 3 wks | 4 wks | 3 mo |
|---|---|---|---|---|---|---|---|
| 2.5 | Appearance | MR | MR | MR | MR | MR | MR |
| | pH | 2.51 | 2.60 | 2.61 | 2.62 | 2.66 | 2.64 |
| | Assay % | 102.2 | 93.1 | 87.4 | 80.8 | 76.9 | 39.6 |
| | Chromatographic purity (%) | 98.39 | 91.03 | 84.48 | 76.82 | 74.60 | 39.94 |
| 2.9 | Appearance | MR | MR | MR | MR | MR | MR |
| | pH | 2.89 | 3.05 | 3.06 | 3.08 | 3.15 | 3.04 |
| | Assay % | 102.5 | 97.4 | 95.7 | 92.5 | 89.9 | 66.4 |
| | Chromatographic purity (%) | 98.79 | 96.08 | 93.45 | 89.76 | 88.09 | 68.11 |
| 3.3 | Appearance | MR | MR | MR | MR | MR | MR |
| | pH | 3.32 | 3.44 | 3.49 | 3.45 | 3.48 | 3.49 |
| | Assay % | 102.8 | 98.4 | 97.2 | 94.6 | 92.1 | 71.3 |
| | Chromatographic purity (%) | 98.90 | 97.62 | 95.62 | 92.85 | 91.07 | 72.19 |
| 3.7 | Appearance | MR | MR | MR | MR | MR | MR |
| | pH | 3.75 | 3.79 | 3.83 | 3.79 | 3.81 | 3.82 |
| | Assay % | 102.6 | 97.1 | 94.8 | 90.0 | 89.7 | 65.4 |
| | Chromatographic purity (%) | 98.93 | 96.98 | 93.18 | 88.367 | 88.79 | 68.18 |
| 4.1 | Appearance | MR | MR | MR | MR | MR | MR |
| | pH | 4.11 | 4.19 | 4.12 | 4.08 | 4.08 | 4.03 |
| | Assay % | 102.8 | 94.5 | 88.4 | 81.7 | 78.5 | 46.6 |
| | Chromatographic purity (%) | 98.97 | 93.50 | 87.05 | 79.73 | 77.08 | 49.87 |
| 4.5 | Appearance | MR | MR | MR | MR | MR | MR |
| | pH | 4.55 | 4.56 | 4.42 | 4.36 | 4.38 | 4.38 |
| | Assay % | 102.3 | 85.7 | 75.9 | 67.9 | 63.2 | 29.9 |
| | Chromatographic purity (%) | 98.95 | 85.27 | 76.46 | 67.20 | 63.10 | 33.15 |

As seen from Table 16, the stability of higher concentration vasopressin formulations in lactate buffer stored at about 50° C. was overall less than other storage conditions. Like the lower concentration formulations, the most stable formulation for storage at about 50° C. has pH 3.3, which was stable by all three tests for more than 4 weeks. The formulations having pH 2.9 and 3.7 were stable at the 2 week time point, but failed the chromatographic test(s) at 3 weeks. The formulations having pH 2.5 and 4.1 were stable for only 1 week and the formulation having pH 4.5 was not stable even for 1 week following storage at about 50° C.

Like the lower concentration formulations discussed above, the high concentration formulations in lactate buffer demonstrated better pH stability over all pH values and storage conditions than did the acetate buffered formulations discussed above, and thus, are preferred for long-term storage compared to acetate buffered solutions.

Example 6—Modeling Shelf-Life Prediction

A shelf-life prediction was modeled for the various pH high concentration formulations in lactate buffer based on the stability data reported in Example 5 above. The modeling was carried out as described in Example 2.

Table 17 below shows the predicted shelf-life for higher concentration vasopressin in lactate buffer formulations based on the stability measurements (chromatographic purity) and the modeling outlined above. Based on the predictions, it is expected that high concentration (100 units/mL) vasopressin formulations in lactate buffer with pH 3.3-3.7 can be stored in the refrigerator (5° C.) for at least 200 months. Formulations having a pH of 3.7-4.1 are expected to be stable when stored refrigerated for up to 140 months.

TABLE 17

Predicted stability (in months) of high concentration vasopressin formulations in lactate buffer at various pHs and storage temperatures

| Temp (° C.) | pH 2.5 | pH 2.9 | pH 3.3 | pH 3.7 | pH 4.1 | pH 4.5 |
|---|---|---|---|---|---|---|
| 5 | 15.0 | 86.6 | 241.4 | 204.1 | 141.8 | 41.9 |
| 25 | 2.4 | 9.8 | 17.0 | 14.0 | 8.5 | 3.5 |
| 30 | 1.5 | 5.9 | 9.3 | 7.6 | 4.5 | 2.0 |
| 40 | 0.7 | 2.3 | 2.9 | 2.4 | 1.3 | 0.7 |
| 50 | 0.3 | 0.9 | 1.0 | 0.8 | 0.4 | 0.2 |

Even when the API is present in a higher concentration, such as, for example, 100 units/mL, the vasopressin in lactate buffer formulations of the present disclosure show improvement in the predicted room temperature (about 25° C.) storage conditions compared to the commercially available (20 units/mL) product in acetate buffer. As seen in Table 17, the model predicts that high concentration vasopressin formulations in lactate buffer will be stable for up to 17 months when formulated at pH 3.3 and stored at 25° C. At pH 3.7, vasopressin in lactate buffer formulations will be stable up to 14 months when stored at 25° C.

Many variations and modifications may be made to the above-described embodiments of the disclosure without departing substantially from the spirit and various principles of the disclosure. All such modifications and variations are intended to be included herein within the scope of this disclosure and protected by the following claims.

What is claimed is:

1. A liquid pharmaceutical composition for intravenous administration comprising:
   i) vasopressin or a pharmaceutically acceptable salt thereof;
   ii) a buffer comprising lactic acid, a lactate salt, or a combination thereof;
   iii) water; and
   iv) optionally, a pH adjuster;
   wherein the pharmaceutical composition has a pH of from about 3.0 to about 4.1; and wherein, as measured by HPLC, the pharmaceutical composition retains 90% or more of the initial concentration of vasopressin or pharmaceutically acceptable salt thereof after storage for at least 18 months when stored at about 25° C. and about 60% relative humidity.

2. The pharmaceutical composition of claim 1 having a pH of from about 3.2 to about 3.4.

3. The pharmaceutical composition of claim 2 having a pH of about 3.3.

4. The pharmaceutical composition of claim 1, wherein the lactate buffer has a concentration of from about 1 to about 20 mM.

5. The pharmaceutical composition of claim 1, wherein the pharmaceutical composition is free of a non-lactate buffer.

6. The pharmaceutical composition of claim 5, wherein the non-lactate buffer is an acetate buffer.

7. The pharmaceutical composition of claim 1, wherein the vasopressin is a vasopressin salt selected from the group consisting of acetate or trifluoroacetate.

8. The pharmaceutical composition of claim 1 further comprising one or more pharmaceutically acceptable excipients.

9. The pharmaceutical composition of claim 8, wherein the one or more pharmaceutically acceptable excipients comprises a preservative.

10. The pharmaceutical composition of claim 1, wherein the composition is free of a preservative.

11. The pharmaceutical composition of claim 1, wherein as measured by HPLC, the pharmaceutical composition retains 90% or more of the initial concentration of vasopressin or pharmaceutically acceptable salt thereof after storage for at least 20 months.

12. The pharmaceutical composition of claim 11 having a pH of from about 3.2 to about 3.4.

13. The pharmaceutical composition of claim 12 having a pH of about 3.3.

14. The pharmaceutical composition of claim 1, wherein, as measured by HPLC, the pharmaceutical composition retains 90% or more of the initial concentration of vasopressin or pharmaceutically acceptable salt thereof after storage for at least 72 months at about 5° C.

15. The pharmaceutical composition of claim 14 having a pH of from about 3.2 to about 3.4.

16. The pharmaceutical composition of claim 15 having a pH of about 3.3.

17. The pharmaceutical composition of claim 1, comprising a concentration of vasopressin or pharmaceutically acceptable salt thereof of between about 0.01 mg/mL and about 0.3 mg/mL.

18. The pharmaceutical composition of claim 17, comprising a concentration of vasopressin or pharmaceutically acceptable salt thereof of between about 0.02 mg/mL and about 0.07 mg/mL.

19. The pharmaceutical composition of claim 17, comprising a concentration of vasopressin or pharmaceutically acceptable salt thereof of between about 0.15 mg/mL and about 0.20 mg/m L.

20. The pharmaceutical composition of claim 1, wherein the composition retains about 95% or more of the initial concentration of vasopressin or pharmaceutically acceptable salt thereof.

21. The pharmaceutical composition of claim 1, wherein, as measured by HPLC, the pharmaceutical composition contains not more than about 2% of an individual degradant after storage at about 5° C. for about 6 months.

22. The pharmaceutical composition of claim 21, wherein, as measured by HPLC, the pharmaceutical composition contains not more than about 1% of an individual degradant after storage at about 5° C. for about 6 months.

23. The pharmaceutical composition of claim 1, wherein, as measured by HPLC, the pharmaceutical composition contains not more than about 3% of an individual degradant after storage at about 25° C. and about 60% relative humidity for about 6 months.

24. The pharmaceutical composition of claim 23, wherein, as measured by HPLC, the pharmaceutical composition contains not more than about 2% of an individual degradant after storage at about 25° C. and about 60% relative humidity for about 6 months.

25. The pharmaceutical composition of claim 1, wherein the pharmaceutical composition is stored in a glass vial.

26. A pharmaceutical composition for intravenous administration consisting of:
   i) between 0.02 mg/mL and 0.05 mg/mL vasopressin or a pharmaceutically acceptable salt thereof;
   ii) a buffer consisting of lactic acid, a lactate salt, or a combination thereof;
   iii) water; and
   iv) optionally, a pH adjuster,
   wherein the pharmaceutical composition has a pH of from about 3.0 to about 3.7; and wherein, as measured by HPLC, the pharmaceutical composition retains 90% or more of the initial concentration of vasopressin or pharmaceutically acceptable salt thereof after storage for at least 18 months when stored at about 25° C. and about 60% relative humidity.

27. The pharmaceutical composition of claim 26, wherein the pH is from about 3.2 to about 3.4.

28. The pharmaceutical composition of claim 27, wherein the pharmaceutical composition retains 90% or more of the initial concentration of vasopressin or pharmaceutically acceptable salt thereof after storage for at least 20 months.

29. A pharmaceutical composition for intravenous administration consisting of:
   i) between 0.15 mg/mL and 0.25 mg/mL vasopressin or a pharmaceutically acceptable salt thereof;
   ii) a buffer consisting of lactic acid, a lactate salt, or a combination thereof;
   iii) water; and
   iv) optionally, a pH adjuster,
   wherein the pharmaceutical composition has a pH of from about 3.0 to about 3.5; and wherein, as measured by HPLC, the pharmaceutical composition retains about 90% or more of the initial concentration of vasopressin or pharmaceutically acceptable salt thereof after storage for about 18 months when stored at about 25° C. and about 60% relative humidity.

30. The pharmaceutical composition of claim 29, wherein the pH is from about 3.2 to about 3.4.

31. The pharmaceutical composition of claim 30, wherein the pharmaceutical composition retains 90% or more of the initial concentration of vasopressin or pharmaceutically acceptable salt thereof after storage for at least 20 months.

32. A method of increasing blood pressure in a patient in need thereof, the method comprising:
a) providing a pharmaceutical composition comprising:
   i) vasopressin or a pharmaceutically acceptable salt thereof;
   ii) a buffer comprising lactic acid, a lactate salt, or a combination thereof;
   iii) water, and
   iv) optionally, a pH adjuster,
   wherein the pharmaceutical composition has a pH of from 3.0 to 4.1; and
   wherein, as measured by HPLC, the pharmaceutical composition retains 90% or more of the initial concentration of vasopressin or pharmaceutically acceptable salt thereof after storage at about 25° C. and 60% relative humidity for about 18 months; and
b) intravenously administering the pharmaceutical composition to the patient.

33. The method of claim 32, wherein the pharmaceutical composition has a pH of from 3.2 to 3.4.

34. The method of claim 33, wherein the pharmaceutical composition has a pH of about 3.3.

35. The method of claim 32, wherein, as measured by HPLC, the pharmaceutical composition retains 90% or more of the initial vasopressin concentration after storage at about 25° C. and 60% relative humidity for about 20 months.

36. The method of claim 35, wherein the pharmaceutical composition retains 90% or more of the initial vasopressin concentration after storage at about 5° C. for about 18 months.

37. The method of claim 32, wherein the pharmaceutical composition is free of a non-lactate buffer.

38. The method of claim 37, wherein the non-lactate buffer is acetate buffer.

39. The pharmaceutical composition of claim 1, wherein the composition is a concentrate requiring dilution prior to administration.

* * * * *